US010233210B2

(12) United States Patent
Tripathi et al.

(10) Patent No.: US 10,233,210 B2
(45) Date of Patent: Mar. 19, 2019

(54) PROCESS FOR PREPARATION OF GLUCOCORTICOID STEROIDS

(71) Applicant: Coral Drugs Pvt. Ltd., New Delhi (IN)

(72) Inventors: Vinayak Tripathi, New Delhi (IN); Rajesh Kumar, New Delhi (IN); Rohit Bhuwania, New Delhi (IN); Binay Kumar Bhuwania, New Delhi (IN)

(73) Assignee: Coral Drugs Pvt. Ltd., New Delhi (IN)

( * ) Notice: Subject to any disclaimer, the term of this patent is extended or adjusted under 35 U.S.C. 154(b) by 0 days.

(21) Appl. No.: 15/543,862

(22) PCT Filed: Jan. 29, 2016

(86) PCT No.: PCT/IN2016/050031
§ 371 (c)(1),
(2) Date: Jul. 14, 2017

(87) PCT Pub. No.: WO2016/120891
PCT Pub. Date: Aug. 4, 2016

(65) Prior Publication Data
US 2018/0002372 A1    Jan. 4, 2018

(30) Foreign Application Priority Data

Jan. 30, 2015   (IN) .............................. 272/DEL/2015

(51) Int. Cl.
*C07J 5/00*       (2006.01)
*C07J 71/00*      (2006.01)
*C07J 13/00*      (2006.01)
*A61K 31/58*      (2006.01)

(52) U.S. Cl.
CPC ........... *C07J 71/0031* (2013.01); *A61K 31/58* (2013.01); *C07J 5/0092* (2013.01); *C07J 13/005* (2013.01); *C07J 71/0015* (2013.01)

(58) Field of Classification Search
CPC ........................ C07J 5/0092; C07J 71/0031
See application file for complete search history.

(56) References Cited

U.S. PATENT DOCUMENTS

| 4,695,625 | A |   | 9/1987 | MacDonald |
| 5,556,964 | A | * | 9/1996 | Hofstraat ............... C07J 5/0092 540/61 |
| 8,158,780 | B2 | * | 4/2012 | Phull ................... C07J 71/0068 540/63 |
| 9,109,005 | B2 | * | 8/2015 | Puder ................... C07J 71/0031 |

FOREIGN PATENT DOCUMENTS

EP    0262108 B1   12/1991
WO    2002038584 A1   5/2002

OTHER PUBLICATIONS

International Search Report and Written Opinion of the ISA/US dated May 31, 2016 in International Application No. PCT/IN2016/050031; 8pgs.

* cited by examiner

*Primary Examiner* — Brenda L Coleman
(74) *Attorney, Agent, or Firm* — Haukaas Fortius PLLC; Michael H. Haukaas

(57) ABSTRACT

The present invention discloses a process for the preparation of 16, 17-acetals of pregnane derivatives having formula I

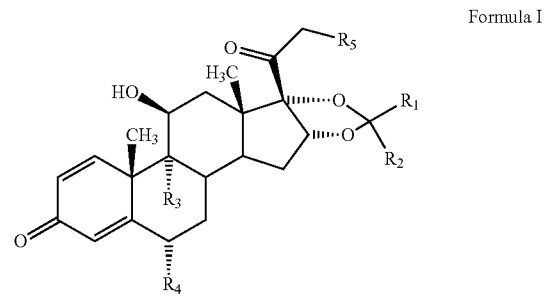

Formula I wherein each substituent is independently selected from;
$R_1$ is H or $CH_3$;
$R_2$ is $C_1$-$C_6$ linear or branched alkyl, alkynyl group or cycloalkyl group; aryl or heteroaryl group; or
$R_1$ and $R_2$ combine to form saturated, unsaturated $C_3$-$C_6$ cyclic or heterocyclic ring;
$R_3$ and $R_4$ are same or different and each independently represents H or halogen;
$R_5$ is —OH or —OCOR wherein R represents H or $C_1$-$C_6$ linear, branched or cyclic alkyl group that may be substituted.

20 Claims, No Drawings

PROCESS FOR PREPARATION OF GLUCOCORTICOID STEROIDS

RELATED APPLICATIONS

This application is a National Stage filing under 35 U.S.C. § 371 of International Application No. PCT/IN2016/050031 filed Jan. 29, 2016, which claims priority to Indian Patent Application No. 272/DEL/2015 filed Jan. 30, 2015, which application is incorporated herein by reference.

FIELD OF THE INVENTION

The present invention provides a synthetic process for the preparation of 16, 17-acetals of pregnane derivatives.

BACKGROUND OF THE INVENTION

Glucocorticoids have a number of diverse effects in different body tissues. Glucocorticoids, in topical, oral and inhaled formulations, are useful for their anti-inflammatory and immunosuppressive properties. Several glucocorticoids such as budesonide and ciclesonide are used for treatment of several disorders.

The synthesis and purification of glucocorticoids have been disclosed at different instances. However, most of these synthetic procedures involve toxic solvents or long reaction times and are ineffective for large scale synthesis. For instance, U.S. Pat. No. 3,929,768 discloses a process for preparation of budesonide by reacting 16, 17-dihydroxy compound with aldehyde in solvents such as dioxane, methylene chloride or their combinations.

DE 4129535 discloses a process for the synthesis of Ciclesonide which involves the intermediate 16A, 17-[(R, S)-cyclohexylmethylenedioxy]-1 13, 21-dihydroxy-pregna-1 4-dien-3,20-one which is obtained by an acid catalysed reaction of 11β, 16α, 17, 21-tetra hydroxypregna-1,4-dien-3,20-one with cyclohexane aldehyde.

WO 02/38584 discloses the synthesis of Ciclesonide by reacting corresponding 16, 17-ketals with a cyclohexane aldehyde in the presence of 70% perchloric acid, 1-nitropropane as solvent. However, perchloric acid is a dangerous solvent and can cause serious accidents with fatal consequences.

U.S. Pat. No. 6,169,178 relates to a process for the preparation of budesonide and of 16, 17-acetals of pregnane derivatives structurally co-related thereto comprising treating 16, 17-dios or of 16, 17-ketals or cyclic acetals with aldehydes in the presence of aqueous hydrobromic acid or hydroiodic acid used as reaction catalyst or solvents. However, hydroiodic and other hydrohalic solvents are corrosive, light sensitive and expensive. Further, these acids also post environmental problems. Notwithstanding the use of hydrohalo acids requires use of special equipment since they are extremely corrosive and consequently increase the cost of production.

U.S. Pat. No. 5,556,964 discloses a process for the preparation of budesonide by reacting 16α-Hydroxy Prednisolone in acetonitrile in the presence of p-toluene sulfonic acid as a catalyst. There are certain other patents that use alkyl sulfonic acid instead of aryl sulfonic acid for the synthesis of budesonide or similar compounds. However, sulfonic acids are hazardous solvents and FDA has expressed significant concern over the presence or traces of sulfonic acid in pharmaceutical products. Hence, there is a need to have a process for the synthesis 16, 17-acetals of pregnane compounds that is industrially scalable and which does not involve the use of harmful solvents.

OBJECT OF THE INVENTION

An object of the present invention is to provide an industrially scalable, viable process for the synthesis of 16, 17-acetals of pregnane compounds without the use of toxic and harmful solvents.

BRIEF DESCRIPTION OF THE INVENTION

The present invention discloses a process for the preparation of 16, 17-acetals of pregnane derivatives having formula I

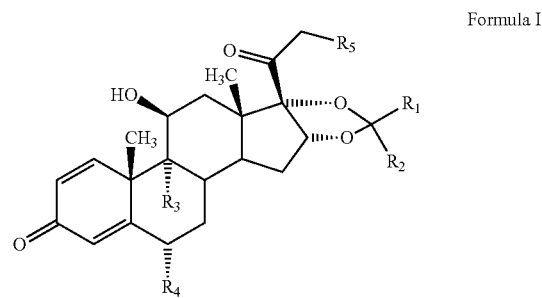

Formula I wherein each substituent is independently selected from;

$R_1$ is H or $CH_3$;

$R_2$ is $C_1$-$C_6$ linear or branched alkyl, alkynyl group or cycloalkyl group; aryl or heteroaryl group; or $R_1$ and $R_2$ combine to form $C_3$-$C_6$ saturated, unsaturated cyclic or heterocyclic ring;

$R_3$ and $R_4$ are same or different and each independently represents H or halogen;

$R_5$ is —OH or —OCOR wherein R represents H or $C_1$-$C_6$ linear, branched or cyclic alkyl group that may be substituted.

The present invention discloses, a novel process for preparing the compounds of formula I;

i. Dihydroxylation of the compound of formula II being 2-((10S,13S,14S)-10,13-dimethyl-3-oxo-6,7,8,10,12,13,14,15-octahydro-3H-cyclopenta[a]phenanthren-17-yl)-2-oxoethyl acetate (3TR) to obtain the compound of formula III ii. Bromination of the compound of formula III to obtain the hydroxylated brominated compound of formula IV iii. Debromination of the compound of formula IV to obtain the compound of formula V iv. Deacetylation of the compound of formula V to obtain the compound of formula VI v. Alkylation of 16, 17-diol of the compound of formula VI to obtain the compound of formula I.

DETAILED DESCRIPTION OF THE INVENTION

The present invention discloses a process for the preparation of 16, 17-acetals of pregnane derivatives having formula I

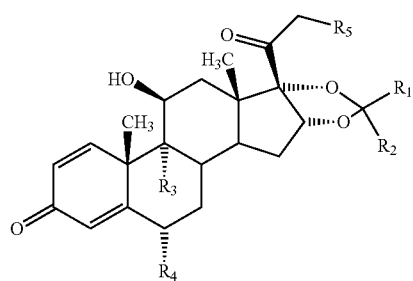

Formula I wherein each substituent is independently selected from;

R₁ is H or CH₃;

R₂ is C₁-C₆ linear or branched alkyl, alkynyl group or cycloalkyl group; aryl or heteroaryl group; or R₁ and R₂ combine to form C₃-C₆ saturated, unsaturated cyclic or heterocyclic ring;

R₃ and R₄ are same or different and each independently represents H or halogen;

R₅ is —OH or —OCOR wherein R represents H or C₁-C₆ linear, branched or cyclic alkyl group that may be substituted. comprising the steps of:

i. dihydroxylation of the compound of formula II 2-((10S,13S,14S)-10,13-dimethyl-3-oxo-6,7,8,10,12,13,14,15-octahydro-3H-cyclopenta[a]phenanthren-17-yl)-2-oxoethyl acetate to obtain the compound of formula III;

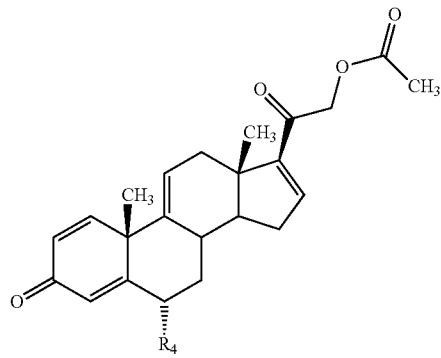

Formula II

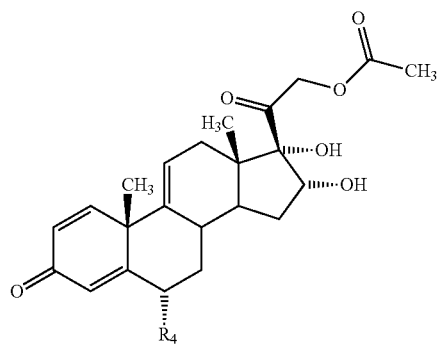

Formula III ii. bromination of the compound of formula III to obtain the hydroxylated brominated compound of formula IV;

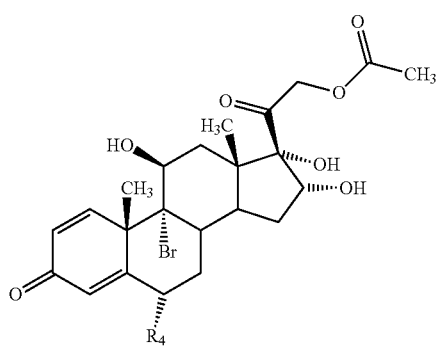

Formula IV iii. debromination of the compound of formula IV to obtain the compound of formula V;

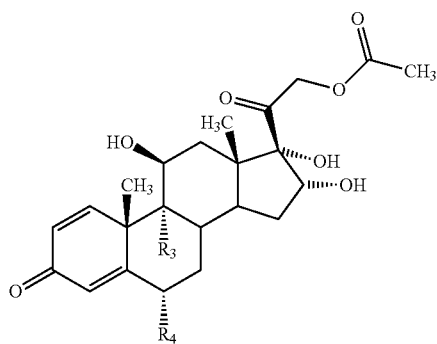

Formula V iv. deacetylation of the compound of formula V to obtain the compound of formula VI;

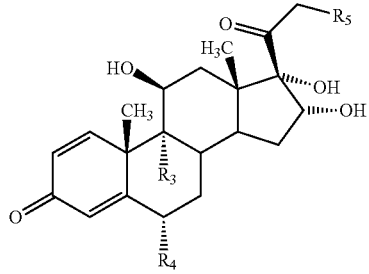

Formula VI v. alkylation of the compound of formula VI to obtain the compound of formula I.

In an embodiment the present invention discloses a process for the preparation of 16, 17-acetals of pregnane derivatives having formula (VII)

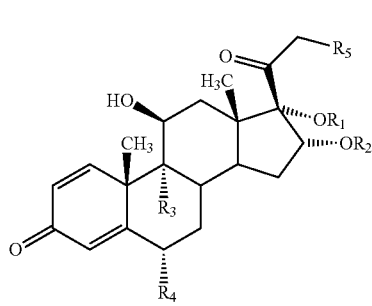

Formula (VII)

wherein $R_1$ and $R_2$ is H;
$R_5$ is OH;
$R_3$ and $R_4$ independently represent H or halogen;

The compounds of formula I and formula VII may include but are not limited to the following compounds as presented at table 1:

TABLE 1

Exemplary compounds of present invention

| Structure | Generic name | IUPAC Name |
|---|---|---|
| 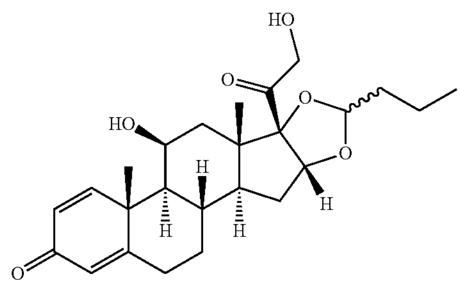 | Budesonide | 16,17-(butylidenebis(oxy))-11,21-dihydroxy-, (11-β,16-α)-pregna-1,4-diene-3,20-dione |
| 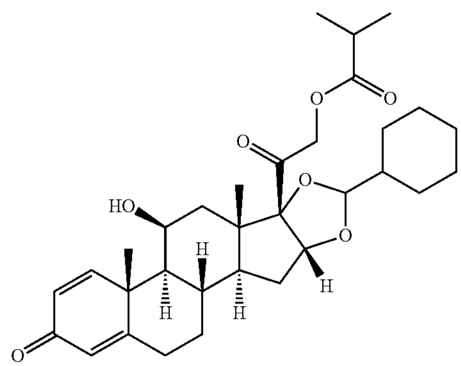 | Ciclesonide | 2-[(1S,2S,4R,8S,9S,11S,12S,13R)-6-cyclohexyl-11-hydroxy-9,13-dimethyl-16-oxo-5,7-dioxapentacyclo [10.8.0.02,9.04,8.013,18] icosa-14,17-dien-8-yl]-2-oxoethyl 2-methylpropanoate. |
| 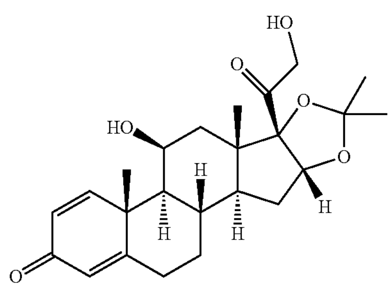 | Desonide | (1S,2S,4R,8S,9S,11S,12S,13R)-11-hydroxy-8-(2-hydroxyacetyl)-6,6,9,13-tetramethyl-5,7-dioxapentacyclo[10.8.0.0$^{2,9}$.0$^{4,8}$.0$^{13,18}$] icosa-14,17-dien-16-one |
| 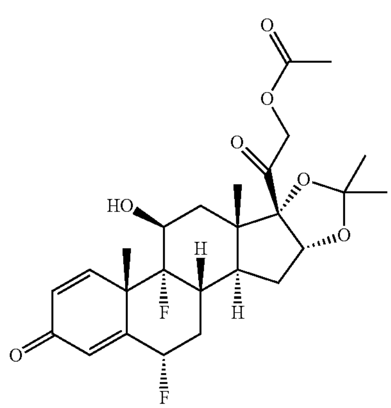 | Fluocinonide | 6α,9-difluoro-11β,16α,17,21-tetrahydroxypregna-1,4-diene-3,20-dione, cyclic 16,17-acetal with acetone, 21-acetate |

TABLE 1-continued

Exemplary compounds of present invention

| Structure | Generic name | IUPAC Name |
|---|---|---|
| 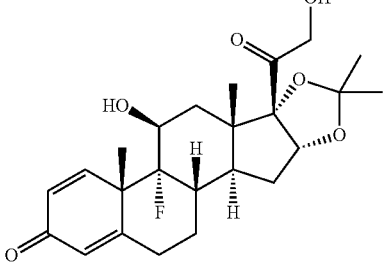 | Triamcinolone acetonide | (4aS,4bR,5S,6aS,6bS,9aR,10aS,10bS)-4b-fluoro-6b-glycoloyl-5-hydroxy-4a,6a,8,8-tetramethyl-4a,4b,5,6,6a,6b,9a,10,10a,10b,11,12-dodecahydro-2H-naphtho[2',1':4,5]indeno[1,2-d][1,3]dioxol-2-one |
| 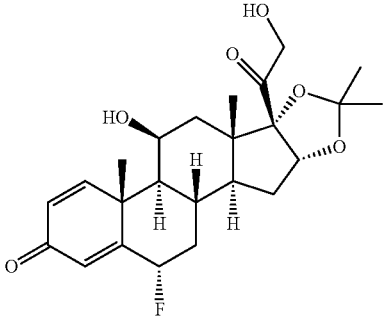 | Flunisolide | 1S,2S,4R,8S,9S,11S,12S,13R,19S)-19-fluoro-11-hydroxy-8-(2-hydroxyacetyl)-6,6,9,13-tetramethyl-5,7-dioxapentacyclo[10.8.0.0$^{2,9}$.0$^{4,8}$.0$^{13,18}$]icosa-14,17-dien-16-one |
| 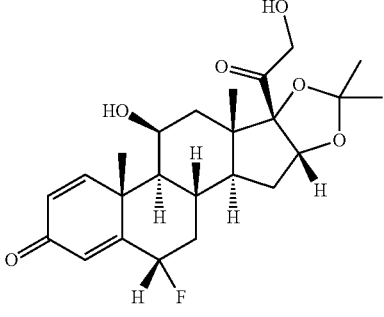 | Fluocinolone acetonide | 1S,2S,4R,8S,9S,11S,12R,13S,19S)-12,19-difluoro-11-hydroxy-8-(2-hydroxyacetyl)-6,6,9,13-tetramethyl-5,7-dioxapentacyclo[10.8.0.0$^{2,9}$.0$^{4,8}$.0$^{13,18}$]icosa-14,17-dien-16-one |
| 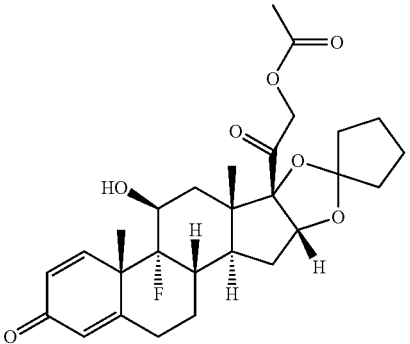 | Amcinonide | 2-[(1S,2S,4R,8S,9S,11S,12R,13S)-12'-fluoro-11'-hydroxy-9',13'-dimethyl-16'-oxo-5',7'-dioxaspiro[cyclopentane-1,6'-pentacyclo[10.8.0.0$^{2,9}$.0$^{4,8}$.0$^{13,18}$]icosane]-14',17'-dien-8'-yl]-2-oxoethyl acetate |
| 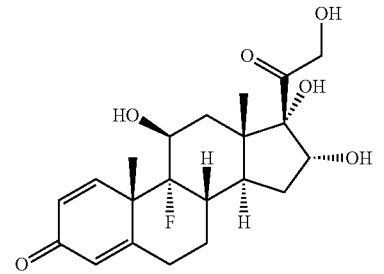 | Triamcinolone | (11β,16α)-9-Fluoro-11,16,17,21-tetrahydroxypregna-1,4-diene-3,20-dione |

TABLE 1-continued

Exemplary compounds of present invention

| Structure | Generic name | IUPAC Name |
|---|---|---|
| 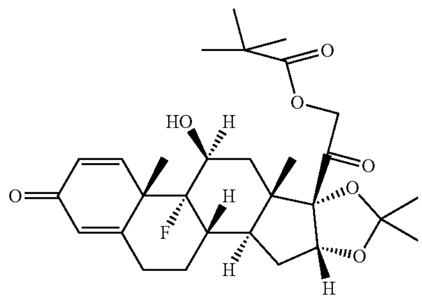 | Triamcinolone hexacetonide | (11β,16α)-21-(3,3-Dimethyl-1-oxobutoxy)-9-fluoro-11-hydroxy-16,17-((1-methylethylidene) bis (oxy))pregna-1,4-diene-3,20-dione |

The compounds of the present invention may be prepared by a process as described herein below:

The process of the present invention is explained at scheme 1.

iv. Deacetylation of the compound of formula V to obtain the compound of formula VI
v. Alkylation of 16, 17-diol of the compound of formula VI to obtain the compound of formula I.

Scheme 1: Process of the present invention

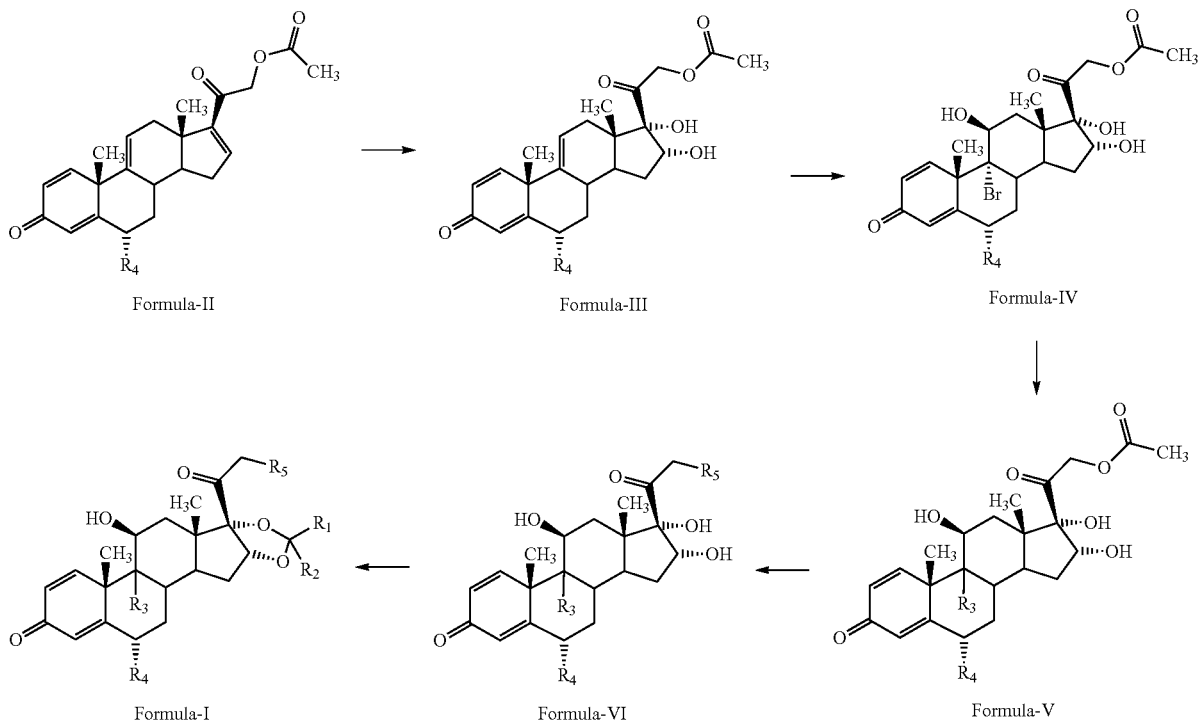

The process of the present invention comprises of the following steps:
i. Dihydroxylation of the compound of formula II being 2-((10S,13S,14S)-10,13-dimethyl-3-oxo-6,7,8,10,12,13,14,15-octahydro-3H-cyclopenta[a]phenanthren-17-yl)-2-oxoethyl acetate (3TR) to obtain the compound of formula III
ii. Bromination of the compound of formula III to obtain the hydroxylated brominated compound of formula IV
iii. Debromination of the compound of formula IV to obtain the compound of formula V The process of the present invention may be suitably started from the compound of formula II, known by its IUPAC name 2-((10S,13S,14S)-10,13-dimethyl-3-oxo-6,7,8,10,12,13,14,15-octahydro-3H-cyclopenta[a]phenanthren-17-yl)-2-oxoethyl acetate and hereinafter referred to as 3TR (formula II).

3TR is suitably dihydroxylated by an oxidizing agent. The oxidizing agent may be selected from the group comprising potassium permanganate, potassium dichromate, chromic acid, peroxyacids or mixtures thereof, preferably potassium permanganate, formic acid and sodium metabisulphite to form compound of formula (III). Under acidic conditions formic acid promotes oxidation reaction and sodium metabisulfite quench the oxidized reaction product to protect the formation of further oxidative impurities in the formulated product. The dihydroxylation of 3TR results in a compound of formula III.

In the present invention, dihydroxylation of compound of formula (II) is carried out with an oxidizing agent, selected from group comprising potassium permanganate, potassium dichromate, chromic acid, peroxyacids or mixtures thereof, preferably potassium permanganate, formic acid and sodium metabisulphite to form compound of formula (III).

The process of the present invention involves the bromination of the compound of formula III to yield the hydroxylated brominated compound of formula IV. The bromination of compound of Formula III may be conducted by suitably reacting the compound of Formula III with a brominating agent selected from the group comprising dibromantin, N-bromosuccinamide etc, preferably dibromantin, in the presence of a solvent. The solvent may be selected from the group comprising tetrahydrofuran, acetone, N, N-dimethyl formamide, DMSO, methanol, methylene dichloride, acetonitrile, ethyl acetate, diethyl ether, 1-butanol, methylethyl ketone, 1-propanol, formamide and the like, preferably tetrahydrofuran.

In the present invention, compound of formula (III) is brominated with a brominating agent, selected from the group comprising dibromantin, N-bromosuccinamide preferably dibromatin to form compound of formula (IV) in presence of organic solvent, selected from the group comprising tetrahydrofuran, acetone, N,N-dimethyl formamide, DMSO, methanol, methylene dichloride, acetonitrile, ethyl acetate, diethyl ether, 1-butanol, methylethyl ketone, 1-propanol, formamide, preferably tetrahydrofuran.

The debromination of compound of formula IV may be conducted in presence of a catalyst, a thiol compound and an aprotic solvent to obtain the compound of formula V.

In the present invention, catalyst is selected from the group comprising chromous or chromium sulfate, chromous or chromium chloride or its hydrate, preferably chromium chloride hexahydrate. The chromium (III) can be recycled to chromium (II) as is known to those skilled in the art. The means for recycling chromium (III) to chromium (II) includes zinc, magnesium, zinc amalgam and magnesium amalgam. Preferred is zinc and magnesium; most preferred is zinc. It is preferred that when the means for recycling is zinc it be present as zinc dust.

Thiols include compounds of the formula $R_t$—SH (Formula VIII). It is preferred that $R_t$ be —$CH_2$—COOH or —$CH_2CH_2$—COOH; it is more preferred that the thiol be thioglycolic (thiovanic) acid where $R_t$ is —$CH_2$—COOH. Improved chemical yields result from the use of greater than 1 equivalent of the thiol, preferably from about 1.5 to about 3.0 equivalents.

In the present invention compound of formula (IV) is debrominated to form compound of formula (V) in presence of catalyst, Rt---SH (VIII) with an aprotic solvent at appropriate temperature, wherein $R_t$—SH  Formula VIII wherein $R_t$ is —$CH_2COOH$ or —$CH_2CH_2COOH$ preferably $R_t$ is —$CH_2COOH$.

Suitable aprotic solvents include DMF, DMAC, acetone, methylene chloride, THF, acetonitrile, DMSO and mixtures thereof. Alcoholic solvents include methanol, ethanol, isopropanol and butanol. Preferred are DMF and DMSO. The temperature is not critical; that temperatures between about −50° C. to about 100° C. are operable and preferred is about room temperature (20° C.-25° C.) or up to about 50° C. Better results can be obtained if the temperature is maintained between −10° and 30° C.

In the present invention, aprotic solvent is selected from the group comprising DMF, DMAC, acetone, methylene chloride, THF, acetonitrile, DMSO and mixtures thereof, preferably DMF and DMSO.

In one embodiment, the compound of formula V may be optionally purified and utilized for commercial purposes. When on C-16 and C-17 of the compound of formula V is "OH", then the compound hydrolyses from 2-oxo-2-((8S, 9S,10R,11S,13S,14S,16R,17S)-11,16,17-trihydroxy-10,13-dimethyl-3-oxo-6,7, 8,9,10,11,12,13,14,15,16,17-dodecahydro-3H-cyclo penta[a]phenanthren-17-yl)ethyl acetate to 16α-Hydroxy Prednisolone (Formula VI), also known as 16-HPN.

The compound of formula V may be converted to compound of formula VI, C-16 and C-17 of the compound of formula V is "OH", then the compound hydrolyses from 2-oxo-2-((8S,9S,10R,11S,13 S,14S,16R,17S)-11,16,17-trihydroxy-10,13-dimethyl-3-oxo-6,7,8,9,10, 11,12,13,14,15, 16,17-dodecahydro-3H-cyclopenta[a]phenanthren-17-yl) ethyl acetate to 16α-Hydroxy Prednisolone (Formula VI), also known as 16-HPN.

In the present invention, compound of formula (V) is deacylated to form compound of formula (VI) 16α-Hydroxy Prednisolone (16-HPN), wherein C-16 and C-17 is OH.

In the present invention, the starting material for the preparation of compound of formula (VI) is compound of formula (II).

In another embodiment, the compound of formula V may be further processed to obtain the compound of formula I. The compound of formula V may be converted to the compound of formula I by the sequential steps of deacetylation and alkylation The same are illustrated at scheme 1 (conversion of formula V to VI and subsequent conversion of formula VI to formula I).

The compound of formula VI may be converted to the compound of formula I by deacetylation and alkylation. The compound of formula VI may be converted to the compound of formula I by reacting with reagents selected from group comprising N-butyraldehyde, cyclohexane carboxaldehyde, sodium metabisulphite complex, isobutyryl chloride, acetone, hydrofluoric acid, isopropenyl acetate, dibromantin, select fluor, perchloric acid, 3,3-dimethyl butyryl chloride and triethylamine or combination, preferably N-butyraldehyde and hydrochloric acid i.e. Budesonide. The epimer A ratio is in range of 54 to 44% at temperature between −5° to −15° C. during addition of N-butyraldehyde and −0° to −10° C. till completion of reaction.

In an embodiment of the present invention the compound of formula (VI) is converted to compound of formula (I) comprising $R_1$ is —H, $R_2$ is —$CH_2CH_2CH_3$, $R_5$ is —OH, by treating with N-butyraldehyde and hydrochloric acid.

In the present invention, the compound of formula (I) comprising $R_1$ is —H, $R_2$ is —$CH_2CH_2CH_3$, $R_5$ is —OH, has desired epimer A ratio in range of 54 to 44% at temperature between −5° to −15° C. during addition of N-butyraldehyde and −0° to −10° C. till completion of reaction.

The compound of formula VI may be converted to the compound of formula I by deacetylation and alkylation. The compound of formula VI may be converted to the compound of formula I by reacting with the reagent selected from the group comprising N-butyraldehyde, cyclohexane carboxaldehyde, sodium metabisulphite complex, isobutyryl chloride, acetone, hydrofluoric acid, isopropenyl acetate, dibromantin, select fluor, perchloric acid, 3,3-dimethyl butyryl chloride and triethylamine or combination, preferably cyclohexane carboxaldehyde is used to form compound of formula I i.e. Ciclesonide.

In an embodiment of the present invention the compound of formula (VI) is converted to compound of formula (I) comprising $R_1$ is —H, $R_2$ is —$C_6H_{11}$, $R_5$ is —OCOCH$(CH_3)_2$, and) is converted to compound of formula (I) by treating with cyclohexane carboxaldehyde, sodium metabisulphite and isobutyryl chloride.

The compound of formula V may be converted to the compound of formula I by reacting with the reagent selected from the group comprising N-butyraldehyde, cyclohexane carboxaldehyde, sodium metabisulphite complex, isobutyryl chloride, acetone, hydrofluoric acid, isopropenyl acetate, dibromantin, select fluor, perchloric acid, 3,3-dimethyl butyryl chloride and triethylamine or combination, preferably acetone and perchloric acid i.e. Desonide.

In an embodiment of the present invention the compound of formula (V) comprising $R_3$ and $R_4$ is H is converted to compound of formula (I) comprising $R_1$ is —$CH_3$, $R_2$ is —$CH_3$, $R_5$ is —OH, by treating with acetone and perchloric acid.

The compound of formula II may be converted to the compound of formula I by reacting with the reagent selected from the group comprising N-butyraldehyde, cyclohexane carboxaldehyde, sodium metabisulphite complex, isobutyryl chloride, acetone, hydrofluoric acid, isopropenyl acetate, dibromantin, select fluor, perchloric acid, 3,3-dimethyl butyryl chloride and triethylamine or combination, preferably acetone, dibromantin, hydrofluoric acid i.e. Triamcinolone acetonide.

In an embodiment of the present invention the compound of formula (II) comprising $R_4$ is H converted to compound of formula (I) comprising $R_1$ is —$CH_3$, $R_2$ is —$CH_3$, $R_5$ is —OH, $R_3$ is —F, $R_4$ is —H, by treating with acetone, dibromantin, hydrofluoric acid.

The compound of formula V may be converted to the compound of formula I by reacting with the reagent selected from the group comprising N-butyraldehyde, cyclohexane carboxaldehyde, sodium metabisulphite complex, isobutyryl chloride, acetone, hydrofluoric acid, isopropenyl acetate, dibromantin, select fluor, perchloric acid, 3,3-dimethyl butyryl chloride and triethylamine or combination, preferably acetone, isopropenyl acetate and select fluor i.e. Flusinolide In an embodiment of the present invention the compound of formula (V) comprising $R_3$ and $R_4$ is H is converted to compound of formula (I) comprising $R_1$ is —$CH_3$, $R_2$ is —$CH_3$, $R_5$ is —OH, $R_3$ is —H, $R_4$ is —F, by treating with acetone, isopropenyl acetate and select fluor.

The compound of formula II may be converted to the compound of formula I by reacting with the reagent selected from the group comprising N-butyraldehyde, cyclohexane carboxaldehyde, sodium metabisulphite complex, isobutyryl chloride, acetone, hydrofluoric acid, isopropenyl acetate, dibromantin, select fluor, perchloric acid, 3,3-dimethyl butyryl chloride and triethylamine or combination, preferably perchloric acid, dibromantin, hydrofluoric acid and 3,3-dimethyl butyryl chloride i.e. Triamcinolone acetonide.

In an embodiment of the present invention the compound of formula (II) comprising $R_4$ is H is converted to compound of formula (I) comprising $R_1$ and $R_2$ is —$CH_3$, $R_5$ is —OH, $R_3$ is —F, $R_4$ is —H, by treating with acetone, isopropenyl acetate and select fluor.

The compound of formula II may be converted to the compound of formula VII by reacting with the reagent selected from the group comprising N-butyraldehyde, cyclohexane carboxaldehyde, sodium metabisulphite complex, isobutyryl chloride, acetone, hydrofluoric acid, isopropenyl acetate, dibromantin, select fluor, perchloric acid, 3,3-dimethyl butyryl chloride and triethylamine or combination, preferably treating with perchloric acid and hydrofluoric acid i.e Triamcinolone.

In an embodiment of the present invention the compound of formula (II) comprising $R_4$ is H is converted to compound of formula (VII) comprising $R_1$ and $R_2$ is H, $R_5$ is —OH, $R_3$ is —F, $R_4$ is —H, by treating with perchloric acid and hydrofluoric acid.

The compound of formula I may be optionally purified to obtain a pure compound. Such purification may be done by means of crystallization or column chromatography.

Advantages of the Present Invention

1. The process of the present invention uses commonly available and inexpensive materials.
2. The process is simple and does not involve any toxic materials.
3. The process yields several intermediates that have biological activity and commercial utility.

The invention will now be further illustrated by non limiting examples.

Working Examples

Example-1: Process for Preparation of 16-HPN from 3TR

Scheme 2: Synthesis of 16HPN from 3TR

Stage-I

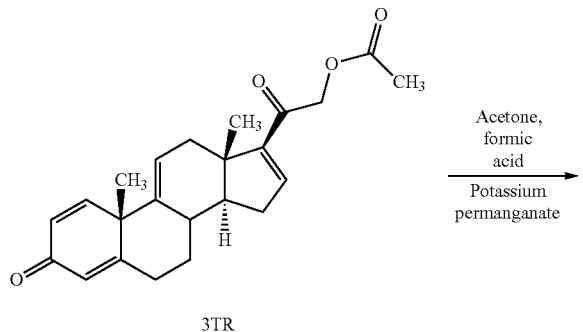

3TR

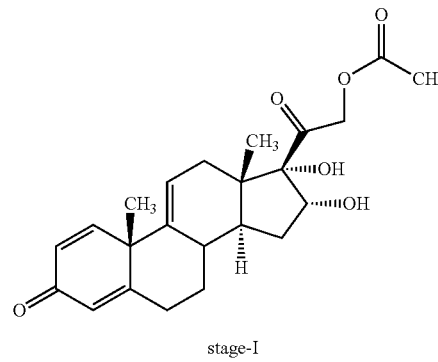

stage-I

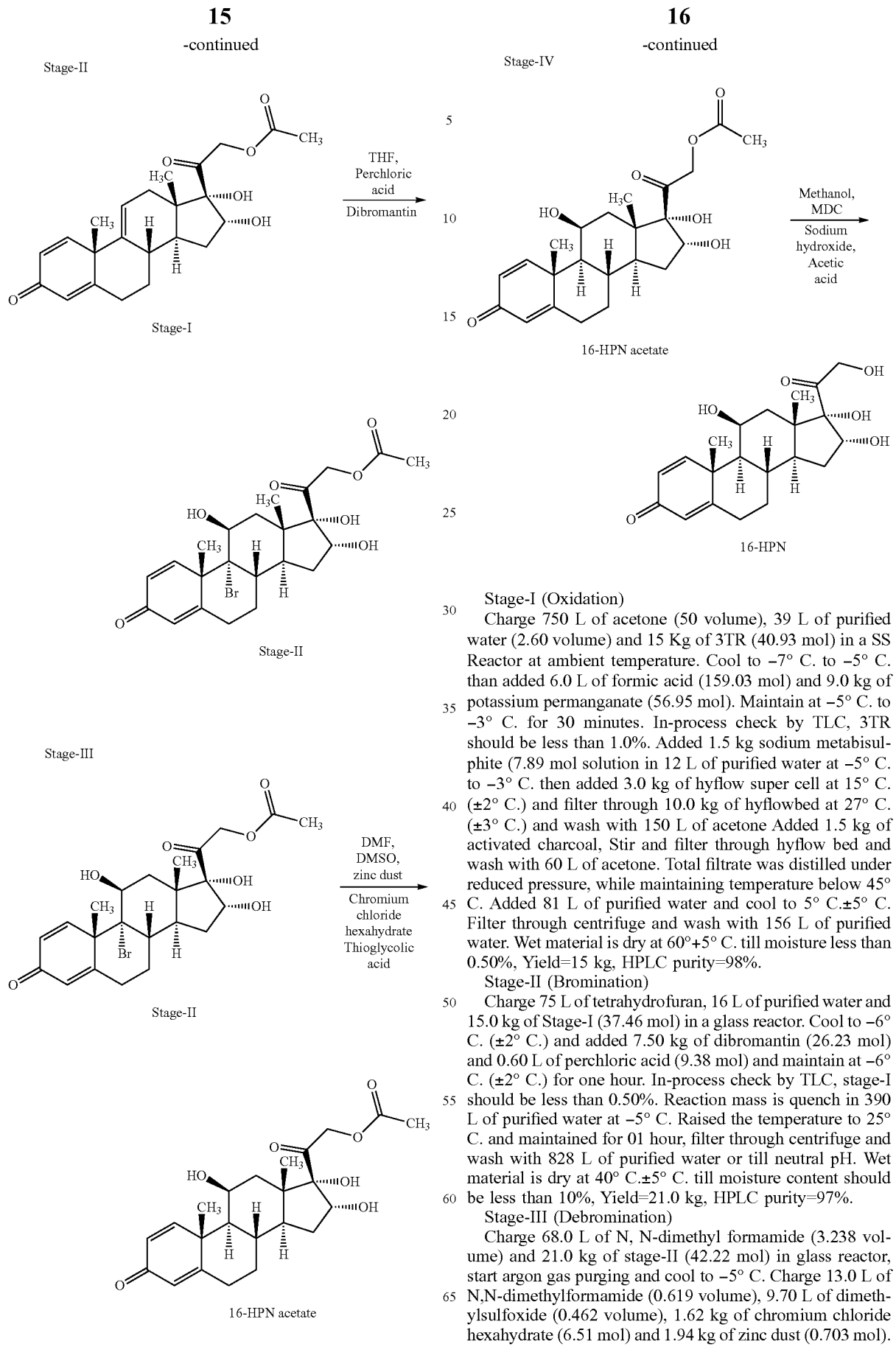

Stage-I (Oxidation)

Charge 750 L of acetone (50 volume), 39 L of purified water (2.60 volume) and 15 Kg of 3TR (40.93 mol) in a SS Reactor at ambient temperature. Cool to −7° C. to −5° C. than added 6.0 L of formic acid (159.03 mol) and 9.0 kg of potassium permanganate (56.95 mol). Maintain at −5° C. to −3° C. for 30 minutes. In-process check by TLC, 3TR should be less than 1.0%. Added 1.5 kg sodium metabisulphite (7.89 mol solution in 12 L of purified water at −5° C. to −3° C. then added 3.0 kg of hyflow super cell at 15° C. (±2° C.) and filter through 10.0 kg of hyflowbed at 27° C. (±3° C.) and wash with 150 L of acetone Added 1.5 kg of activated charcoal, Stir and filter through hyflow bed and wash with 60 L of acetone. Total filtrate was distilled under reduced pressure, while maintaining temperature below 45° C. Added 81 L of purified water and cool to 5° C.±5° C. Filter through centrifuge and wash with 156 L of purified water. Wet material is dry at 60°+5° C. till moisture less than 0.50%, Yield=15 kg, HPLC purity=98%.

Stage-II (Bromination)

Charge 75 L of tetrahydrofuran, 16 L of purified water and 15.0 kg of Stage-I (37.46 mol) in a glass reactor. Cool to −6° C. (±2° C.) and added 7.50 kg of dibromantin (26.23 mol) and 0.60 L of perchloric acid (9.38 mol) and maintain at −6° C. (±2° C.) for one hour. In-process check by TLC, stage-I should be less than 0.50%. Reaction mass is quench in 390 L of purified water at −5° C. Raised the temperature to 25° C. and maintained for 01 hour, filter through centrifuge and wash with 828 L of purified water or till neutral pH. Wet material is dry at 40° C.±5° C. till moisture content should be less than 10%, Yield=21.0 kg, HPLC purity=97%.

Stage-III (Debromination)

Charge 68.0 L of N, N-dimethyl formamide (3.238 volume) and 21.0 kg of stage-II (42.22 mol) in glass reactor, start argon gas purging and cool to −5° C. Charge 13.0 L of N,N-dimethylformamide (0.619 volume), 9.70 L of dimethylsulfoxide (0.462 volume), 1.62 kg of chromium chloride hexahydrate (6.51 mol) and 1.94 kg of zinc dust (0.703 mol).

Cool to −10° C. and added 5.50 L of thioglycolic acid (79.21 mol). Maintain for one hour while maintaining temperature around −10° C. In-process check by TLC, stage-II should be less than 1.0%. Added 310 L of purified water and cool to 0° C. Filter through centrifuge and wash with 1600 L of purified water. Wet material is dry at 60° C.±(5° C.) till moisture content less than 6.0%, Yield=15.0 kg, HPLC Purity=90%.

Charge 150 L of methylene chloride (10 volume), 150 L of methanol (10 volume.) and 15.0 kg (30.16 mol) of stage-III in a SS Reactor. Heat to clear solution then added 3.0 kg of activated charcoal (20%) and reflux for 04 hours, Filter through hyflow bed and wash with 75 L of methylene chloride (5 volume), and 75 L of methanol (5 volume) mixture. Total filtrate is distilled till last drop and added 75 L (5 volume) of methylene dichloride, reflux for 04 hours than cool to 40° C.±(5° C.), Filter through centrifuge and wash with 15 L (one volume) of methylene chloride. Wet material is dry at 60° C. (±5° C.) till moisture contents less than 1.0% (Yield=13.0 kg, HPLC Purity=96%). Further charge 65.0 L (5 volume) of ethyl acetate and 13.0 kg (1.0 mol) of purified material. Heat to reflux and maintain for 04 hours under reflux, then cool to 40° C. Filter through centrifuge and wash with 13.0 L (one volume) of ethyl acetate. Wet material is dry at 60° C. (±5° C.) till moisture contents less than 0.50%, Yield=12.0 kg, HPLC Purity=98.6%.

Stage-IV (Deacetylation)

Charge 5.83 L of methanol (10 volume) and 5.83 L of methylene chloride (10 volume) in a glass flask and added 583 gm of 16-HPN acetate (1.397 mol) at RT. Start argon gas purging and cool to 0° C. to 5° C. under argon purging. Prepare 11.66 gm of sodium hydroxide (0.2915 mol) solution in 0.583 L of methanol (one volume) under argon purging and cool to 0° C. to 5° C. Sodium hydroxide solution is charge in reaction mass at 0° C. to 5° C. Maintained the reaction mass at 0° C. to 5° C. for one hour, In-process check by TLC against 16-HPN acetate it should be nil. Adjust pH to neutral by 21.40 ml of acetic acid (0.3742 mol); distill under reduced pressure while maintaining temperature below 40° C., till dry. Cool to ambient temperature and added 1.166 L of purified water (02 volume). Cool to 0° C. and maintain for one hour. Filter and wash with 300 ml of purified water. Dry at 60° C. (±5° C.) till moisture content less than 1.0%, Yield=490 gm (93.50%), HPLC Purity=98.97%, Single impurity=0.40%.

Example 2: Process of Synthesis of Budesonide from 16-HPN

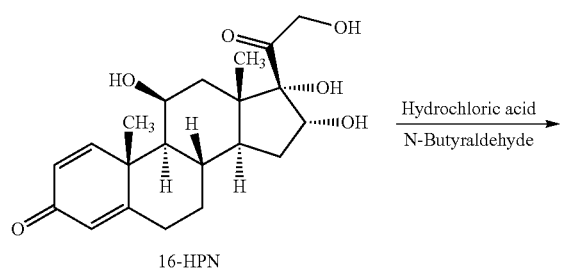

Charge 800 ml of aqueous hydrochloric acid (8 volume) in a glass flask, start nitrogen gas purging and Cool to −5° C. and maintain for 15 min. then added 100 gm of stage-I (0.27 mol) at −5° C. and stir for 15 min., added 30 ml of N-butyraldehyde (0.33 mol) while maintaining temperature −5° C. to 0° C. in around 30 minutes and maintain at 0° C. to 5° C. for 150 min. under stirring. In-process check by TLC against stage-I, it should be nil. Reaction mass is quench in 1200 ml of purified water (12 volume) at 5° C. to 10° C. and stir for 15 min. Added solution of 100 kg of sodium bicarbonate (1.19 mol) and 1 ml of purified water (10 volume) in reaction mass at 5° C. to 10° C. Stir at 5° C. to 10° C. for 15 min. Filter and wash with purified water till neutral pH. Wet material is dry at 50° C. (±5° C.) till moisture contents less than 1.0%, Yield=110 gm (96.49%), HPLC purity=96.45%, single impurity=1.29%, Epimer-A=47.76%, Epimer-B=49.69%.

(Purification)

Charge 2.5 L of methanol (25 volume) in a Glass flask and added 100 gm of above mentioned crude product. Dissolved at 25° C.±5° C. till clear solution, added 10 gm of activated charcoal and stir for 30 min. than filter through hyflow bed and wash with 200 ml of methanol (2 volume). Combined filtrates charged in a Glass flask and cool to 10° C. to 15° C. and added 5.40 L of purified water (54 volume) at 5° C. to 10° C., stir for 15 min., filter and wash with purified water. Wet material is dry at 50° C. (±5° C.) under vacuum till moisture content less than 0.50%, Output=90.0 gm, HPLC purity=99.66%, single impurity=0.1%, Epimer-A=44.47%, Epimer-B=55.01%.

Example 2.1: Scale-Up Process of Manufacturing of Budesonide from 16-HPN

Charge 40 L of aqueous hydrochloric acid (8 volume) in a glass flask, start nitrogen gas purging and Cool to −10° C. and maintain for 15 min. then added 5.0 kg of stage-I (13.315 mol) at −10° C. and stir for 45 min. added 1.5 L of N-butyraldehyde (16.68 mol) while maintaining temperature −7° C. to −11° C. in around 30 minutes and maintain at −2° C. to −6° C. for 60 min. under stirring In-process check by TLC against stage-I, it should be nil. Reaction mass is quench in 60 L of purified water (12 volume) at 5° C. to 10° C. and stir for 15 min. Added solution of 5.0 kg of sodium bicarbonate (59.525 mol) and 50 L of purified water (10 volume) in reaction mass at 5° C. to 10° C. Stir at 5° C. to 10° C. for 15 min. Filter and wash with purified water till neutral pH. Wet material is dry at 50° C. (±5° C.) till moisture contents less than 1.0%, Yield=5.293 kg (94.46%), HPLC purity=95.45%, single impurity=1.45%, Epimer-A=53.51%, Epimer-B=43.78%

Effect of Temperature and its Variation on Epimer Ratio (A and B) with Respect to Batch Size (from Lab to Commercial Batch)

The results are shown in Table 1:

TABLE 1

Comparative data of budesonide Lab development and Plant batches

| Exp. No./ Batch No. | Input | Output | Reaction temperature during addition of N-butyraldehyde | Addition time | Temperature/ time after addition till completion | Time duration | Results (Isomer ratio) Remarks | |
|---|---|---|---|---|---|---|---|---|
| | | | | | | | Epimer-A | Epimer-B |
| 14020 | 0.10 kg | 0.11 kg | (−)5° C. to 0° C. | ~30 min | 0° C. to 5° C./150 min | 150 Min. | 49.69% | 46.76% |
| 14021 | 0.10 kg | 0.11 kg | (−)5° C. to 0° C. | ~30 min | 0° C. to 5° C./150 min | 150 Min. | 44.34% | 51.09% |
| 14022 | 2.00 kg | 2.22 kg | (−)5° C. to 0° C. | ~30 min | 0° C. to 5° C./150 min | 150 Min. | 35.29% | 62.51% |
| 14023 | 2.00 kg | 2.22 kg | (−)7° C. to (−) 11° C. | ~30 min | (−) 2° C. to (−) 6° C./60 min | 60 Min. | 50.54% | 45.94% |
| 3612-14005 | 5.0 Kg | 5.293 kg | (−)7° C. to (−) 11° C. | ~30 min | (−) 2° C. to (−) 6° C./60 min | 60 Min. | 53.51% | 43.78% |
| 3612-14006 | 5.0 Kg | 5.273 kg | (−)7° C. to (−) 11° C. | ~30 min | (−) 2° C. to (−) 6° C./60 min | 60 Min. | 53.34% | 43.42% |
| 3612-14007 | 5.0 Kg | 5.283 kg | (−)7° C. to (−) 11° C. | ~30 min | (−) 2° C. to (−) 6° C./60 min | 60 Min. | 52.20% | 44.19% |

From the results in table, it is clear that epimer ratio of A and B is maintained at 0 to −5° C. on lab scale but not on pilot or commercial batch. However as the batch size increases there is substantial variation in epimer ratio at 0 to −5° C. Therefore, this temperature is not suitable for scale up and industrial use. But at temperature −7 to −11° C. the epimer ratio is maintained (within normal standard deviation limits) at pilot as well as commercial batch. In addition, it may be noted that when optimum parameters of temperature and other parameters as set out herein the reaction time is reduced to 60 minutes from 120. Therefore, reducing the cost and increasing the economic viability and industrial applicability.

Example 3: Process for Synthesis of Ciclesonide from 16HPN

Preparation of Cyclohexane Carboxaldehydemetabisulphite Complex 200 gm of Cyclohexane carboxaldehyde (1.786 mol) was dissolved in 3.0 L of denatured sprit (15 volume) and a solution of 190 gm of sodium metabisulphite (1.827 mol) in 300 ml of purified water (1.5 volume) was added. The resulting precipitate was filtered and washed with 1.0 L of denatured sprit (5.0 volume) and dried under vacuum at 50° C., till moisture content less than 6.00%, Yield=400 gm (97%)

Stage I: Preparation of Stage-I from 16-HPN

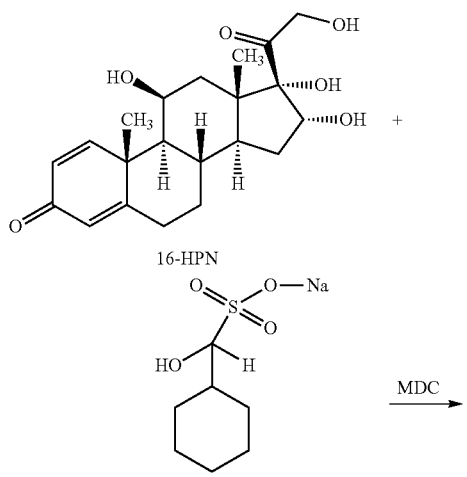

16-HPN

Cyclohexane carboxaldehyde sodium metabisulphite complex

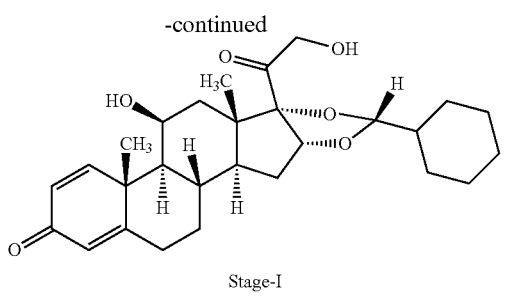

Stage-I 170 gm of 16-HPN (0.4528 mol) was suspended in 3.40 L of dichloromethane (20 volume) and treated with 340 ml of 70% perchloric acid. (5.65 mol) and 110.5 gm of cyclohexane carboxaldehyde metabisulphite complex (0.512 mol) was added in lots while maintaining the temperature between 0° C. to 5° C. The reaction mass was stirred at 0° C. to 5° C. for 03 hours. In-process check by TLC 16-HPN should be nil and then neutralized with 10% aqueous sodium bicarbonate solution. The organic layer was separated and concentrated under vacuum to obtain a residue which was stripped with methanol (1.0 volume). The solvent was concentrated and the residue was dissolved by refluxing in methanol (5.0 volume). The clear solution was cooled to 0° C. to 5.0° C. and the resulting solid was filtered and dried at 50° C. till moisture content less than 0.50%, Yield=170.0 gm (80.0%), HPLC purity=91.68%.

Stage-II Preparation of Ciclesonide from Stage-I

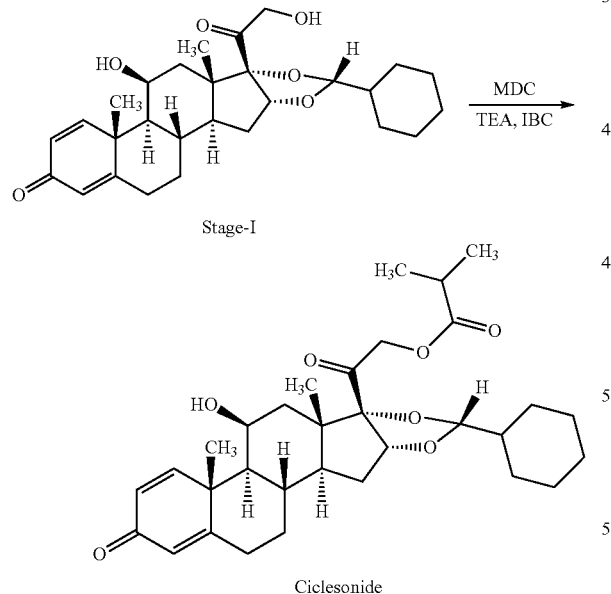

Ciclesonide 158 gm of stage-I (0.34 mol) was suspended in 1.58 L of methylene chloride (10.0 volume) at 25° C. to 30° C. The reaction mass was chilled to 0° C. to 5° C. and 81.0 ml of triethylamine (0.581 mol) was added, followed by the addition of 79.0 ml of isobutyryl chloride [0.75 mol; diluted with 79.0 ml of methylene chloride (0.50 volume)] slowly at 0° to 5° C. and maintained at same temperature for 60 min. In-process check by TLC, Stage-I should be nil. The reaction mass was diluted with 2.53 L of purified water (16.0 volume), the organic layer was separated and washed with purified water till neutral pH, than organic layer was separated and concentrated under vacuum to obtained a residue. The residue was dissolved by refluxing in 948 ml of methanol (6.0 volume); the clear solution was cooled to 0° C. to 5° C. under stirring and filtered. The product was dried under vacuum at −50° C. till moisture contents comes less than 0.50%, Yield=158.0 gm (87.0%), HPLC purity=95.74%.

(Purification)

120 gm of Ciclesonide crude was dissolved by refluxing in 600 ml of methanol. The clear solution was chilled to 20° C. under stirring and filtered. The product was dried under vacuum at 90° C. till moisture content less than 0.50%. Yield=105 gm (87.50%), HPLC purity=99.7%.

Example 4: Process for Synthesis of Desonide from 16HPN Acetate

Stage-I: Preparation of Desonide Acetate from 16 HPN Acetate

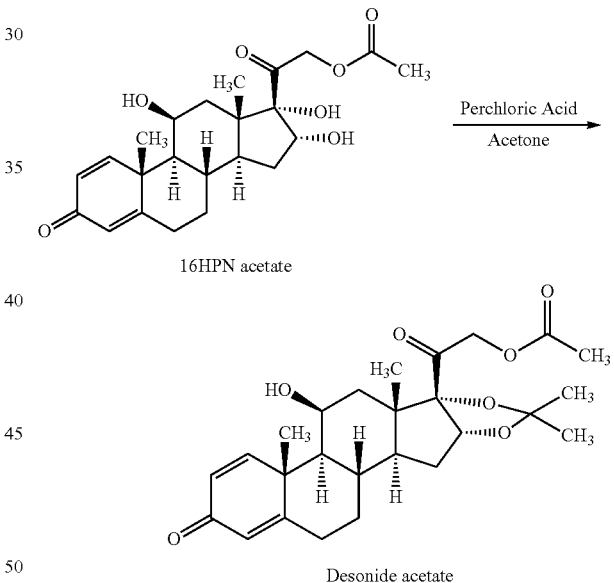

Desonide acetate 190.0 ml of acetone (7.0 volume) was charged in a glass flask under nitrogen blanketing than added 27 gm of 16HPN acetate (0.0645 mol) at ambient temperature. Temperature raised to 28° C. (±2° C.) and stir for 20 minutes. 1.35 ml of perchloric acid 70% (0.021 mol) was added at 28° C. (±2° C.) and stir for 30 minutes. Temperature further raised to 35° C. and stir for 60 minutes. In-process check by TLC against 16HPN acetate, it should be nil. Reaction mass cooled to 10° C., filtered and washed with purified water till neutral pH (~7) and finally washed with acetone. Wet material dried at 50° C.±5° C. till moisture content less than 0.50% to get stage-I. Yield=23 gm (77.76%), HPLC Purity=98.28%

Stage-II: Preparation of Desonide from Desonide Acetate

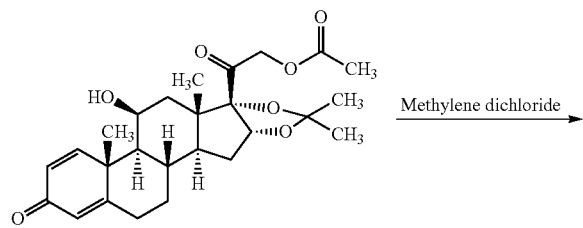

200 ml of methanol (10 volume) and 200 ml of methylene dichloride (10 volume) was charged in a glass flask and start argon gas purging. 20 gm of stage-$1^{st}$ (0.0436 mol) was added at ambient temperature. Cool to 0° C.±5° C. 0.40 gm of sodium hydroxide (0.01 mol) solution in 20 ml of methanol (1.0 volume) was added at 0° C.±5° C. Stir at 0° C.±5° C. for 120 minutes. In-process check by TLC against stage-$1^{st}$ it should be nil. Adjust pH to neutral (~7) by 2.0 ml of acetic acid at 0° C.±5° C. Distilled the solvent from reaction mass under vacuum while maintaining temperature below 40° C. till the volume get reduced to 3 to 4 volume of the input. Cool to 0° C. and further added 60 ml of purified water and stir for 30 minutes. Filtered, washed with purified water till neutral pH (~7). Wet material dried at 50° C.±5° C. till moisture content less than 0.50% to get crude Desonide. Yield=14.70 gm (80.92%), HPLC Purity=88.15%.

(Purification)

140 ml of methanol (10 volume) and 140 ml of methylene chloride (10 volume) was charged in a glass flask and added 14.0 gm of crude material (0.034 mol) than stir till clear solution. Added 1.5 gm of activated charcoal and stir for 30 minutes than filtered through hyflow supercel bed and washed with 30 ml of methanol and 30 ml of methylene chloride mixture. Combined filtrate and distilled the solvent from reaction mass under vacuum while maintaining temperature below 40° C. till the volume reduced to 3 to 4 volume of the input. Cool to 0° C. Filtered the reaction mass and washed with 10 ml of precooled methanol. Wet material was dried at 50° C.±5° C. till moisture content less than 0.50% to get Desonide. Yield=8.60 gm, HPLC Purity=99.43%

Example 5: Process for Synthesis of Triamcinolone Acetonide from 3TR

Stage-I:

100 gm of 3TR (0.27 mol.) was suspended in 1300 ml (13 volume) acetone. Cooled it to −5° C. to −10° C. than added 4.0 ml (0.062 mol.) perchloric acid solution and 50 gm of dibromantin. Maintained the reaction at same temperature for 02 hours. In-process check by TLC against 3TR it should be nil. Added 100 gm of potassium carbonate solution (0.723 mol.) in 5 lots and reaction was maintained at 35° C.±2° C. In-process check by TLC against step-I reaction mass, it should be nil. Cooled to 0° C. (±5° C.) and adjust pH neutral (~7) by 36 ml of acetic acid (0.63 mol.). Added 3.0 L of purified water (30 volume). Filter and washed with purified water till neutral pH (~7). Wet material was dried at 45° C. (±2° C.) till moisture content less than 0.50%. Yield=87 gm, (83.36%), HPLC Purity=97.883%.

Stage-II:

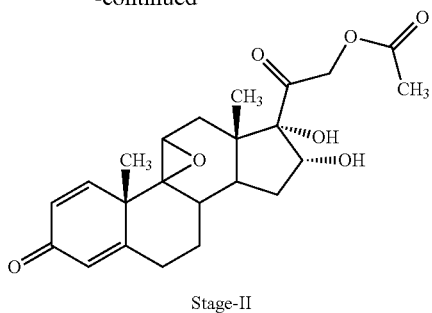

Stage-II 80 gm of stage-I (0.21 mol) was dissolved in 4.0 L of acetone (50 volume) and 208 ml of purified water (2.6 volume). Cool to −5° C. (±2° C.) than added 32 ml of formic acid (0.85 mol.) and 48 gm of potassium permagnate (0.30 mol.) at −5° C. (±2° C.). Reaction was maintained at −5° C.±2° C. for one hour. In-process check by TLC against stage-I it should be nil. Added 8 gm of sodium metabisulphite (0.042 mol.) In 80 ml purified water (01 volume) solution at −5° C. (±2° C.). Temperature raised up to 27° C. and filtered through hyflow bed and washed with acetone. Acetone was distilled under vacuum till 3 to 4 volume of stage-I than cool to 0° C. to 5° C. and added 480 ml of purified water stir and filter and washed with purified water to get wet stage-II. Wet material was dried at 50° C. (±5° C.) till moisture content less than 3.0%. Yield=78.30 gm, (89.88%), HPLC Purity=99.178%.

Stage-III:

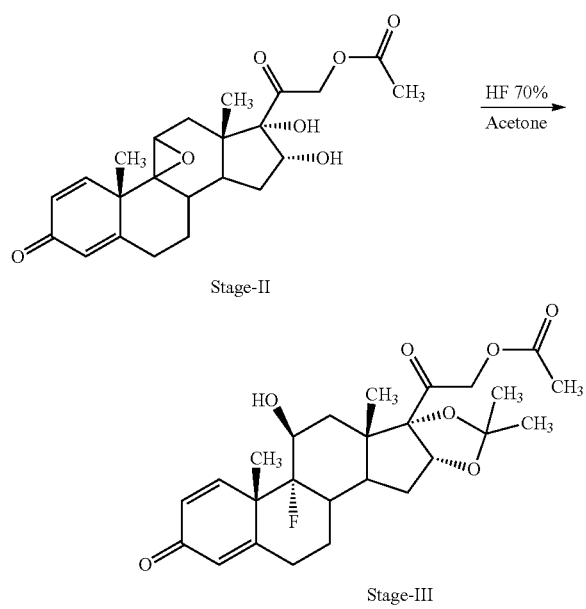

300 ml of hydrofluoric acid (12.60 mol) was cooled at −25° C. to −30° C. than added 75 gm of stage-II (0.180 mol). Reaction was maintained at −25° C. to −30° C. for 04 hours. In-process check by TLC against stage-II, it should be nil. Reaction mass was cooled to −50° C. than added 45 ml of acetone (0.60 volume) at −45° C. to −50° C. Reaction was maintained at −45° C. to −50° C. for 02 hours. In-process check by TLC against before acetone reaction mass. Added 565 ml of purified water at 0° C. and 340 ml of liq. ammonia at ~20° C. than reaction mass was quenched in 410 ml of liq. ammonia and 735 ml of purified water solution at 15° C. (±2° C.), stir and filter and washed with purified water till neutral pH. Wet material was dried at 45° C. to 50° C., Yield=78.50 gm, (91.48%), HPLC Purity=91.593%.

(Purification)

76 gm of stage-III Crude (0.16 mol.) was dissolved in 760 ml of methylene chloride (10 volume) and 760 ml of methanol (10 volume) mixture at ambient temperature. Stir till clear solution and added 7.6 gm of activated charcoal (0.10 volume) than stir for 30 minutes, filter through hyflow bed and washed with methanol (one volume) and methylene chloride (one volume) mixture. Total filtrate was distilled under vacuum till 3 to 4 volume of input. Cool to 0° C. to 5° C. and stir for 02 hours. Filtered and washed with minimum precooled methanol, Wet material was dried 45° C. to 50° C. till moisture contents less than 0.50%, Yield=62 gm, HPLC Purity=98.633%.

Stage-IV (Process for Synthesis of Triamcinolone Acetonide from Stage-III):

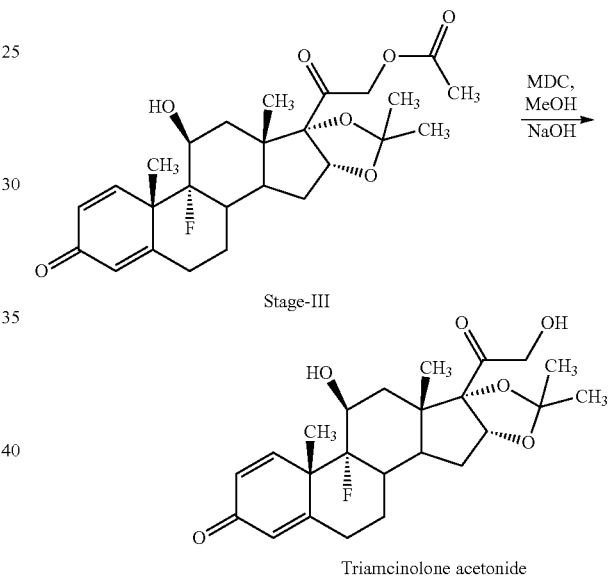

60 gm of stage-III (0.13 mol) was dissolved in 600 ml of methanol (10 volume) and 600 ml of methylene chloride (10 volume) mixture under argon bubbling. Cool to −5° C.±2° C. and added 1.2 gm of sodium hydroxide (0.03 mol.) solution in 60 ml of methanol (01 volume) at −5° C. (±2° C.). Reaction maintained at −5° C. (±2° C.) for 03 hours. In-process check by TLC against stage-III, it should be nil. Adjust pH neutral (~7) by adding 1.8 ml of acetic acid at −5° C. (±2° C.). Reaction mass was distilled at below 40° C. under vacuum till 3 to 4 volume of input. Cool to 30° C. and added 120 ml of purified water, stir for one hour than filter and washed with purified water till neutral pH (~7). Wet material was dried at 45° C. to 50° C. till moisture content less than 0.50%, Yield=52 gm, (95.04%), HPLC Purity=99.21%

(Purification)

50 gm of crude material (0.12 mol.) was dissolved in 1100 ml of acetone (22 volume) and 100 ml of purified water (02 volume) at 50° C. than added 2.5 gm of activated charcoal and stir for one hour at same temperature, Filter through hyflow bed and washed with 120 ml of acetone (2.40 volume). Filtrate was distilled below 40° C. under vacuum till 3 to 4 volume of input. Cool to 0° C. to 5° C. and maintained for one hour at same temperature. Filter and washed with water. Wet material was dried at 45° C. to 50° C. till moisture content less than 0.50%, Yield=43 gm, HPLC Purity=99.40%.

Example 6: Process for Synthesis of Flunisolide from 16HPN Acetate

Stage-I (Preparation of Desonide Acetate from 16HPN Acetate):

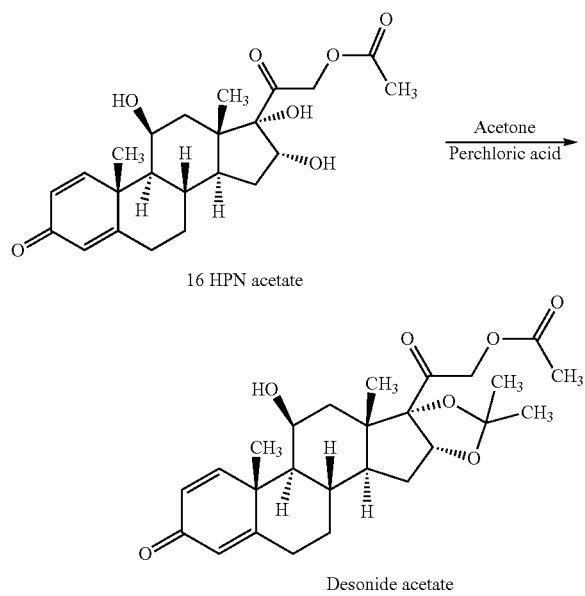

16 HPN acetate

Desonide acetate 140 ml of acetone (7 volume) was charged in glass flask and start argon blanketing than added 20 gm of 16-HPN acetate (0.048 mol) at ambient temperature. Cooled to 28° C. (±2° C.). 1.0 ml of perchloric acid 70% (0.016 mol) was added at 28° C. (±2° C.) and stirred for 30 minutes. Temperature raised up to 35° C. and stirred for 60 minutes. In-process check by TLC against 16-HPN acetate, it should be nil. Reaction mass was cooled to 10° C. (±2° C.). Reaction mass was filtered and washed with purified water till neutral pH (~7) to get wet material. Wet material was dried at 50° C.±5° C. till moisture content less than 0.50% to get stage-$1^{st}$ Yield=17.40 gm, (79.40%), HPLC Purity=98.241%.

Stage-II (Preparation of Desonide from Desonide Acetate):

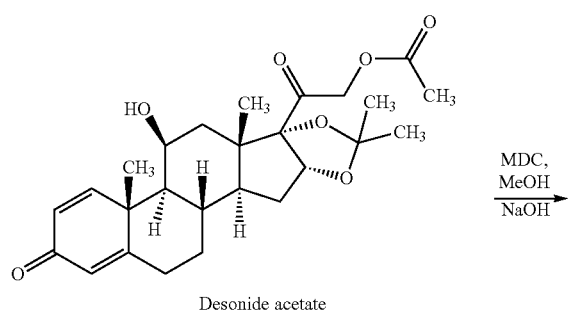

Desonide acetate

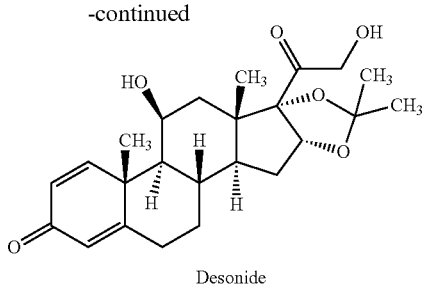

Desonide 170 ml of methanol (10 volume) and 170 ml of methylene chloride (10 volume) was charged in a glass flask and start inert atmosphere. 17 gm of stage-$1^{st}$ (0.037 mol) was added at ambient temperature. Cooled to –5° C. 0.4 gm of sodium hydroxide (0.01 mol) solution in 17 ml of methanol was added at 0° C. (±5° C.). Reaction mass was stirred for 02 hours at 0° C. (±5° C.). In-process check by TLC against stage-$1^{st}$ it should be nil. Neutral pH (~7) was adjusted by acetic acid. Reaction mass was distilled under vacuum at below 40° C. till ~100 ml. Concentrated mass was cooled to 0° C. (±5° C.) and stir for one hour. Reaction mass was filtered and washed with precooled methanol to get wet material. Wet material was dried at 50° C. (±5° C.) till moisture content less than 0.50% to get stage-$2^{nd}$. Yield=14.0 gm, (90.67%), HPLC Purity=99.426%, Single impurity=0.136%.

Stage-III (Preparation of Flunisolide Acetate from Desonide):

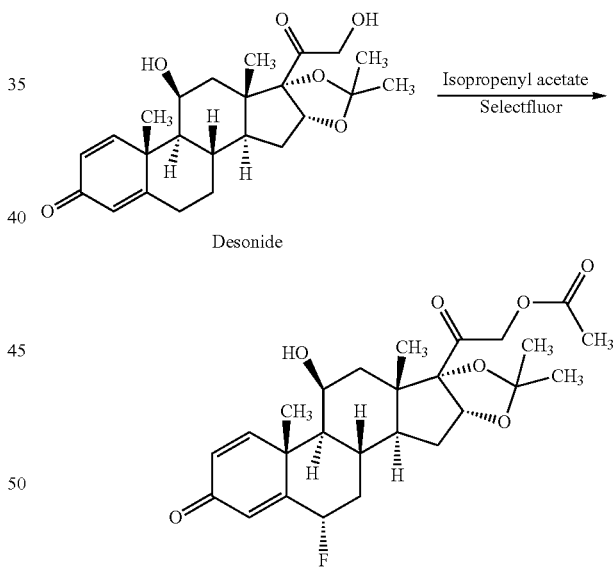

Desonide

Flunisolide acetate 50 ml of isopropenyl acetate (5 volume) was charged in a glass flask and added 10 gm of stage-$2^{nd}$ (0.024 mol) at ambient temperature than heated to 65° C. and added 1.5 ml of methane sulphonic acid (0.023 mol) and temperature raised up to 80° C. and stir for one hour. In-process check by TLC against stage-2, it should be nil. Reaction mass cooled to 25° C. and adjust pH neutral (~7) by triethylamine. Reaction mass was distilled under vacuum till last drop and degases with acetonitrile. 90 ml of acetonitrile (09 volume) was added and cooled to –5° C. and than further added 10 ml of purified water. 10 gm of selectfluor (0.028 mol) was added in two lots at 0° C. (±5° C.) in 02 volume of acetonitrile. Reaction mass was stirred at 10° C. to 15° C. for 12 hours. In-process check by TLC against before selectfluor reaction mass it should be nil. Adjust pH neutral (~7) by liq. ammonia solution at 0° C.±5° C. Reaction mass was quenched in 500 ml of purified water (100 volume) at ambient temperature. Reaction mass was filtered and washed with purified water till neutral pH (~7). Wet material was dried at 45° C.±5° C. till moisture content less than 0.50% to get stage-3rd. Yield=8.60 gm, (75.17%), HPLC Purity=94.12%.

Stage-IV (Preparation of Flunisolide from Flunisolide Acetate):

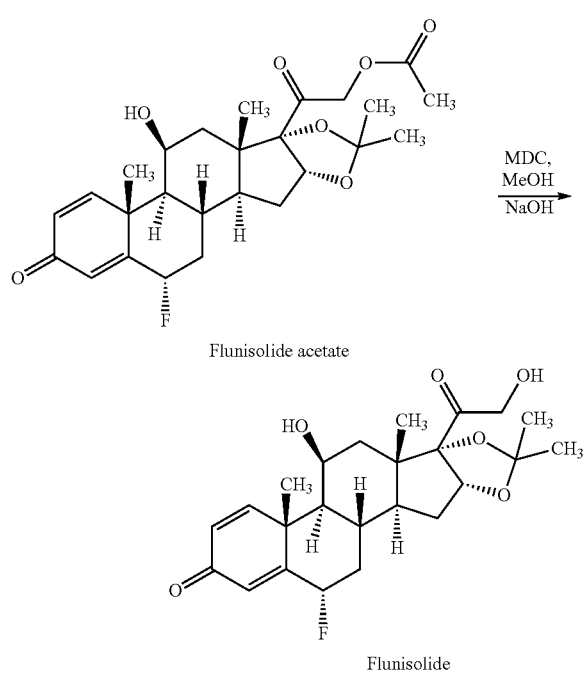

80 ml of methanol (10 volume) and 80 ml of methylene chloride (10 volume) was charged in a glass flask under inert atmosphere at ambient temperature than added 8.0 gm of stage-3$^{rd}$(0.017 mol) at ambient temperature. Cooled to −5° C. and added 0.16 gm of sodium hydroxide (0.004 mol) solution in 8 ml of methanol at −5° C. (±5° C.) and stir for 02 hours at −5° C. (±5° C.). In-process check by TLC against stage-3$^{rd}$, it should be nil. Adjust pH neutral (~7) by acetic acid and reaction mass was distilled under vacuum at below 40° C. (±5° C.) till ~40 ml of volume. Cool to 0° C. to 5° C. and stir for one hour. Reaction mass was filtered and washed with precooled methanol to get wet material. Wet material was dried at 45° C. (±5° C.) till moisture content less than 0.50% to get Flunisolide crude. Yield=6.0 gm, (82.30%), HPLC Purity=86.50%.

(Purification)

6.0 gm of crude Flunisolide (0.014 mol) was dissolved in 65 ml of ethyl acetate (10.83 volume) and 35 ml of n-hexane (5.83 volume) mixture and clear solution was passed through 60 gm of silica gel column. Column was washed with 975 ml of ethyl acetate (162.5 volume) and 525 ml of n-hexane (87.5 volume) mixture. Eluted fraction was distilled under vacuum till 3 to 4 volume of input than cooled it to 0° C. and filter to get wet material. Wet material was dried at 50° C. (±5° C.) till moisture content less than 0.50% to get Flunisolide. Yield=4.28 gm, HPLC Purity=95.60%.

Example 7: Process for Synthesis of Triamcinolone from 3TR

Stage-I:

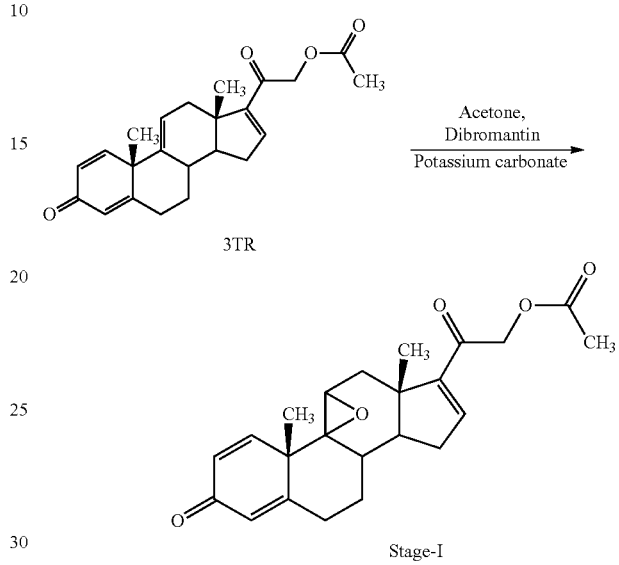

100 gm of 3TR (0.27 mol) was suspended in 1300 ml (13 volume) acetone. Cool to −5° C. to −10° C. than added 4.0 ml (0.062 mol) perchloric acid solution and 50 gm of dibromantin. Reaction maintained at same temperature for 02 hours. In-process check by TLC against 3TR, it should be nil. Added 100 gm of potassium carbonate solution (0.723 mol) in 5 lots and reaction was maintained at 35° C. (±2° C.). In-process check by TLC against step-I reaction mass, it should be nil. Cool to 0° C.±5° C. and adjust pH neutral (~7) by 36 ml of acetic acid (0.63 mol). Added 3.0 L of purified water (30 volume). Filter and washed with purified water till neutral pH (~7). Wet material was dried at 45° C. (±2° C.) till moisture content less than 0.50% to get stage-I. Yield=85.30 gm, (81.74%), HPLC Purity=96.54%.

Stage-II:

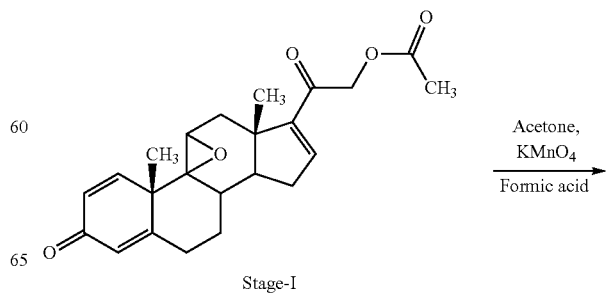

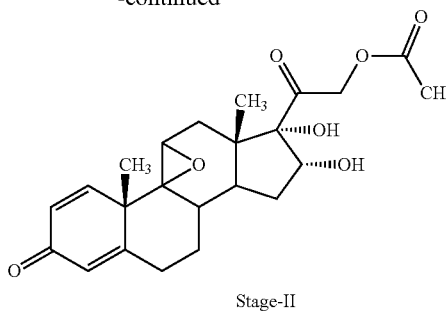

Stage-II 80 gm of stage-I (0.21 mol) was dissolved in 4.0 L of acetone (50 volume) and 208 ml of purified water (2.6 volume). Cool to −5° C. (±2° C.) than added 32 ml of formic acid (0.85 mol.) and 48 gm of potassium per magnate (0.30 mol) at −5° C. (±2° C.). Reaction was maintained at same temperature for one hour. In-process check by TLC against stage-I, it should be nil. Added sodiummetabisulphite solution (8 gm in 80 ml of water) at −5° C.±2° C. Temperature was raised up to 27° C. and filtered through hyflow bed and washed with acetone. Acetone was distilled under vacuum till 3 to 4 volume of stage-I than further cooled to 0° C. to 5° C. and added 480 ml of purified water, stirred, filter and washed with purified water to get wet stage-II. Wet material was dried at 50° C. (±5° C.) till moisture content less than 3.0% to get stage-II. Yield=82 gm, (94.13%), HPLC Purity=97.75%.

Stage-III:

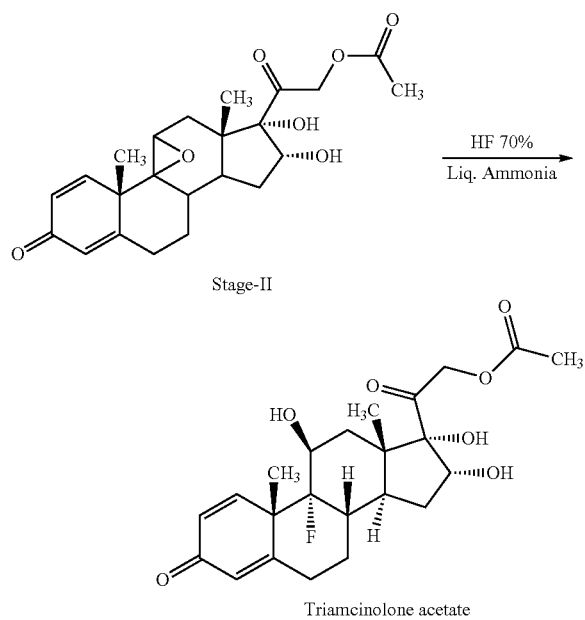

Triamcinolone acetate 160 ml of hydrofluoric acid (70%) (6.72 mol) was cooled at −25° C. to −30° C. than added 40 gm of stage-II (0.096 mol). Reaction was maintained at −25° C. to −30° C. for 04 hours. In-process check by TLC against stage-II, it should be nil. Added 280 ml of purified water at 0° C. and 650 ml of liq. ammonia at 20° C. than reaction mass was quenched in 200 ml of liq. ammonia and 500 ml of purified water solution at 15° C. (±2° C.), stirred, filtered and washed with purified water till neutral pH (~7). Wet material was dried at 45° C. to 50° C. to get stage-III Yield=40 gm, (95.42%), HPLC Purity=88.71%

(Purification)

40 gm of stage-III crude (0.0916 mol) was refluxed in 160 ml of acetone. Cool to 0° C. Filtered and washed with minimum precooled acetone. Wet material was dried at 50° C.±5° C. till moisture content comes less than 0.50% to get stage-III. Yield=24.9 gm HPLC Purity=95.17%.

Stage-IV (Preparation of Triamcinolone from Stage-III):

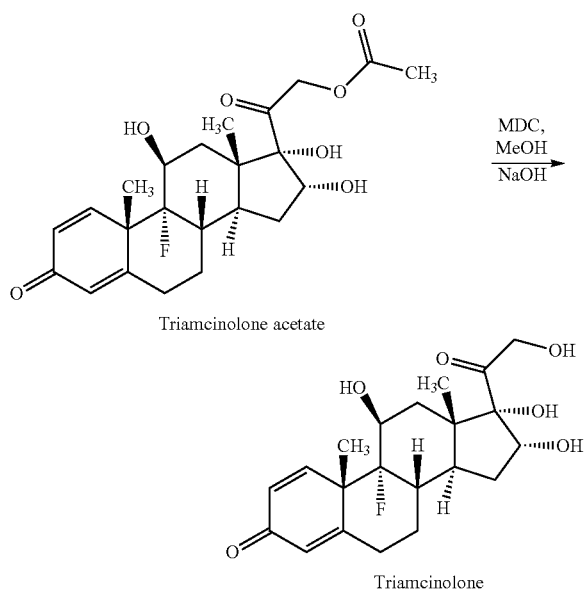

24 gm of stage-III (0.055 mol) was dissolved in 240 ml of methanol (10 volume) and 240 ml of methylene chloride (10 volume) mixture under argon bubbling. Cool to −5° C.±2° C. and added 0.48 gm of sodium hydroxide (0.012 mol) solution in 24 ml of methanol (01 volume) at −5° C.±2° C. Reaction was maintaining at −5° C. (±2° C.) for 03 hours. In-process check by TLC against stage-III, it should be nil. Adjust pH neutral by adding 0.70 ml of acetic acid at −5° C. (±2° C.). Reaction mass distilled at below 40° C. under vacuum till 04-05 volume of input. Cooled to 0° C.±5° C. and stir for one hour than filtered and washed with minimum precooled methanol. Wet material was dried at 45° C. to 50° C. till moisture content less than 0.50%. Yield=18.50 gm, (85.29%), HPLC Purity=98.60%.

Example 8: Process for Synthesis of Triamcinolone Hexacetonide from 3TR

Stage-I:

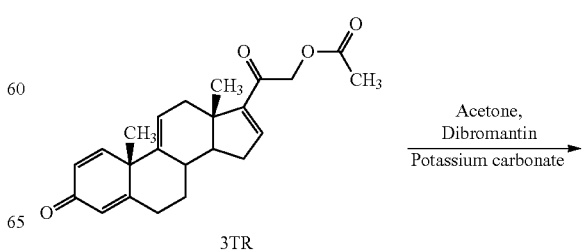

3TR

Stage-I:

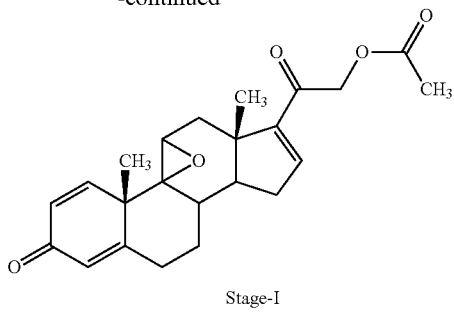

Stage-I 100 gm of 3TR (0.27288 mol) was suspended in 1300 ml (13 volume) acetone. Cool to −5° C. to −10° C. than added 4.0 ml (0.0625 mol) perchloric acid solution and 50 gm of dibromantin. Reaction was maintained at same temperature for 02 hours. In-process check by TLC against 3TR, it should be nil. Added 100 gm of potassium carbonate solution (0.723 mol) in 5 lots and reaction was maintained at 35° C. (±2° C.). In-process check by TLC against step-I reaction mass, it should be nil. Cool to 0° C. (±5° C.) and adjust pH neutral (~7) by 36 ml of acetic acid (0.63 mol). Added 3.0 L of purified water (30 volume). Filter and washed with purified water till neutral pH. Wet material was dried at 45° C. (±2° C.) till moisture content less than 0.50% to get stage-1$^{st}$. Yield=87 gm, (83.36%), HPLC Purity=97.883%.

Stage-II:

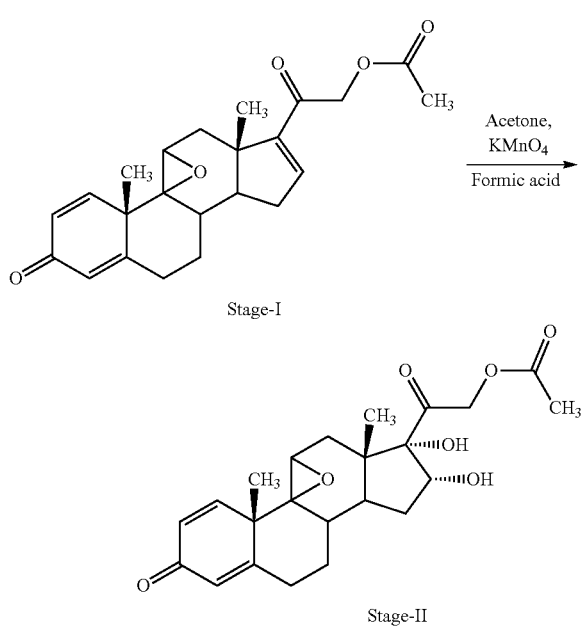

80 gm of stage-I (0.21 mol) was dissolved in 4.0 L of acetone (50 volume) and 208 ml of purified water (2.6 volume). Cool to −5° C. than added 32 ml of formic acid (0.85 mol.) and 48 gm of potassium permanganate (0.30 mol) at −5° C.±2° C. Reaction maintained at −5° C. (±2° C.) for one hour. In-process check by TLC against stage-I, it should be nil. Added sodium metabisulphite solution (8 gm in 80 ml water) at −5° C. (±2° C.). Temperature raised up to 27° C. and filtered through hyflow bed and washed with acetone. Acetone was distilled under vacuum till 3 to 4 volume of stage-I than cooled to 0° C. to 5° C. and added 480 ml of purified water, stirred, filtered and washed with purified water to get wet stage-II. Wet material was dried at 50° C. (±5° C.) till moisture content less than 3.0% to get stage-2nd. Yield=78.30 gm, (89.88%), HPLC Purity=99.18%.

Stage-III:

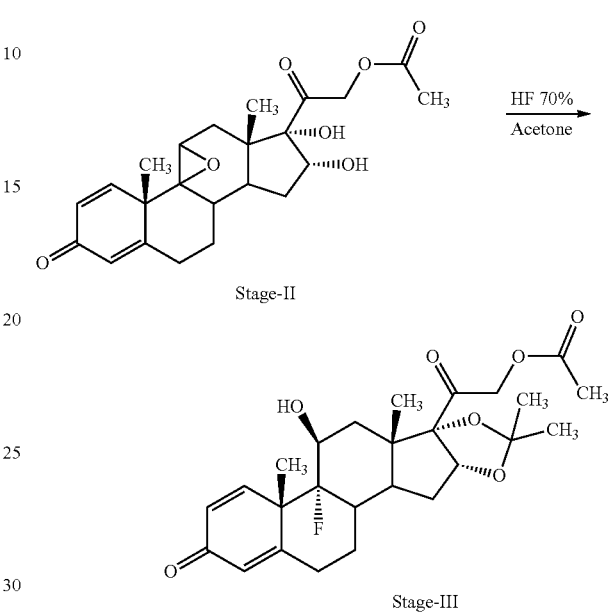

300 ml of hydrofluoric acid (12.60 mol) was cooled at −25° C. to −30° C. than added 75 gm of stage-II (0.180 mol). Reaction was maintained at −25° C. to −30° C. for 04 hours. In-process check by TLC against stage-II. It should be nil. Reaction mass was cooled to −50° C. than added 45 ml of acetone (0.60 volume) at −45° C. to −50° C. Reaction maintained at −45° C. to −50° C. for 02 hours. In-process check by TLC against reaction input, it should be nil. Added 565 ml of purified water at 0° C. and 340 ml of liq. ammonia at 20° C. than reaction mass was quenched in 410 ml of liq. ammonia and 735 ml of purified water solution at 15° C.(±2° C.), stirred, filtered and washed with purified water till neutral pH (~7). Wet material was dried at 45° C. to 50° C. to get stage-3rd. Yield=78.50 gm, (91.48%), HPLC Purity=91.59%.

(Purification)

76 gm of stage-III Crude (0.16 mol) was dissolved in 760 ml of methylene chloride (01 volume) and 760 ml of methanol (10 volume) mixture at ambient temperature. Stirred till clear solution and added 7.6 gm of activated charcoal (0.10 volume) than further stir for 30 minutes and filtered through hyflow bed and washed with methanol (one volume) and methylene chloride (one volume) mixture. Total filtrate was distilled under vacuum till 3 to 4 volume of input. Cooled to 0° C. to 5° C. and stir for 02 hours. Filtered and washed with minimum precooled methanol. Wet material was dried at 45° C. to 50° C. till moisture content less than 0.50% to get purified stage-3$^{rd}$. Yield=62 gm, HPLC Purity=98.633%

Stage-IV: (Preparation of Triamcinolone Acetonide from Stage-III)

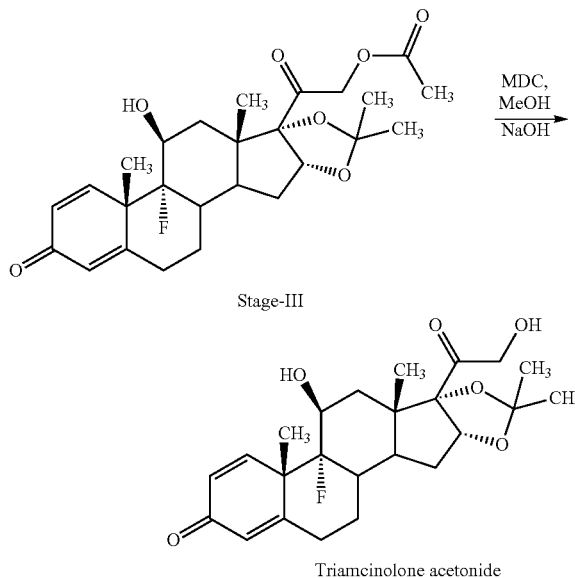

Stage-III

Triamcinolone acetonide

Stage-V: (Preparation of Triamcinolone Hexacetonide from Triamcinolone Acetonide):

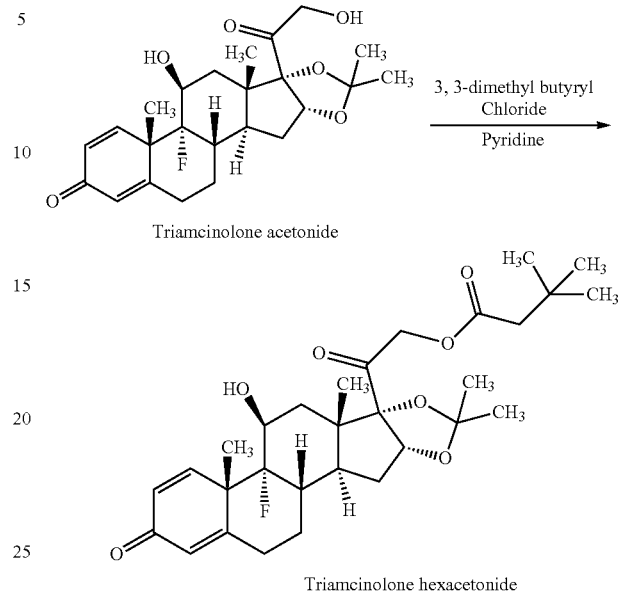

Triamcinolone acetonide

Triamcinolone hexacetonide 60 gm of stage-III (0.1259 mol) dissolved in 600 ml of methanol (10 volume) and 600 ml of methylene chloride (10 volume) mixture under inert atmosphere. Cool to −5° C. and added 1.2 gm of sodium hydroxide (0.03 mol) solution in 60 ml of methanol (01 volume) at −5° C. (±2° C.). Reaction maintained at −5° C.±2° C. for 03 hours. In-process check by TLC against stage-III, it should be nil. Adjust pH neutral (~7) by adding 1.8 ml of acetic acid at −5° C.±2° C. Reaction mass was distilled below 40° C. under vacuum till 3 to 4 volume of input. Cool to 30° C. and added 120 ml of purified water, stir for one hour than filtered and washed with purified water till neutral pH (~7). Wet material was dried at 45° C. to 50° C. till moisture content less than 0.50% to get stage-4$^{th}$ (Triamcinolone acetonide). Yield=52 gm, (95.04%), HPLC Purity=99.21%.

(Purification)

50 gm of crude material (0.12 mol) dissolved in 1100 ml of acetone (22 volume) and 100 ml of purified water (02 volume) at 50° C. than added 2.5 gm of activated charcoal and stirred for one hour at same temperature. Filter through hyflow bed and washed with 120 ml acetone (2.40 volume). Filtrate was distilled below 40° C. under vacuum till 3 to 4 volume of input. Cool to 0° C. to 5° C. and maintained for one hour at same temperature. Filtered and washed with water. Wet material was dried at 45° C. to 50° C. till moisture content less than 0.50% to get purified stage-4$^{th}$. Yield=43 gm, HPLC Purity=99.40%

50 ml of pyridine (10 volume) charged in a glass flask and added 10 gm of Triamcinolone acetonide (0.023 mol) at ambient temperature. Heated to 80° C. to 90° C. than added 10 ml of 3, 3-dimethyl butyryl chloride (0.1 mol) at 80° C. to 90° C. Stirred at 80° C. to 90° C. for 02 hours. In-process check by TLC against Triamcinolone acetonide, it should be nil. Reaction mass cooled to ambient temperature and reaction mass was quenched in 1000 ml of purified water (100 volume) at ambient temperature, stir for one hour than filtered and washed with purified water till neutral pH (~7). Wet material was dried at 50° C. (±5° C.) till moisture content less than 1.0% to get stage-5$^{th}$ (Triamcinolone Hexacetonide). Yield=12 gm, (97.90%), HPLC Purity=98.63%.

(Purification)

120 ml of methanol and 120 ml of methylene chloride charged in a glass flask and added 12 gm of crude material, stir till clear solution than added 1.2 gm of activated charcoal and stir for 30 minutes. Filtered through hyflow bed and washed with 12 ml of methanol and 12 ml of methylene chloride mixture. Total filtrate was distilled under vacuum at below 40° C. till 5 to 6 volume of crude. Cooled to 0° C.±5° C. and stir for one hour. Filtered and washed with 12 ml of precooled methanol. Wet material was dried at 40° C.±5° C. till moisture content less than 0.50% to get Trimcinolne-Hexacetonide. Yield=8.8 gm, HPLC Purity=99.625%

We claim:

1. A process for the preparation of 16,17-acetals of pregnane derivatives having formula (I)

Formula I

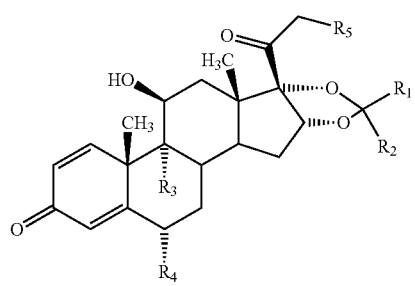

wherein:

$R_1$ is H or $CH_3$;

$R_2$ is $C_1$-$C_6$ linear or branched alkyl, alkynyl group or cycloalkyl group, aryl or heteroaryl group; or $R_1$ and $R_2$ combine to form a saturated or unsaturated $C_3$-$C_6$ cyclic or heterocyclic ring;

$R_3$ and $R_4$ are the same or different and each independently represents H or halogen; and $R_5$ is —OH or —OCOR wherein R represents H or $C_1$-$C_6$ linear, branched or cyclic alkyl group that is optionally substituted; comprising the steps of:

(i) dihydroxylation of the compound of formula II to obtain the compound of formula III;

Formula II

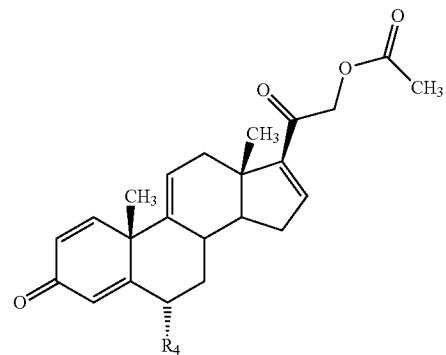

Formula III

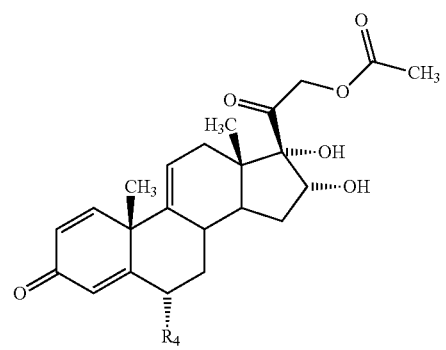

(ii) bromination of the compound of formula III to obtain the hydroxylated brominated compound of formula IV;

Formula IV

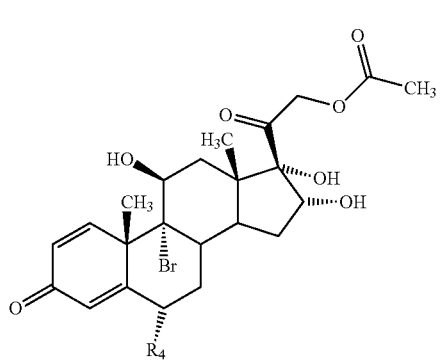

(iii) debromination of the compound of formula IV to obtain the compound of formula V;

Formula V

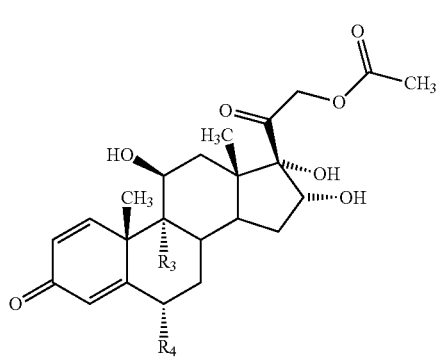

(iv) deacetylation of the compound of formula V to obtain the compound of formula VI;

Formula VI

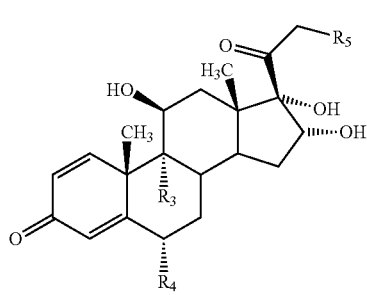

and (v) alkylation of the compound of formula VI to obtain the compound of formula I.

2. The process as claimed in claim 1, wherein in step (i) dihydroxylation of compound of formula (II) is carried out with an oxidizing agent selected from potassium permanganate, potassium dichromate, chromic acid, peroxyacids, formic acid, and sodium metabisulphite, or mixtures thereof, to form a compound of formula (III).

3. The process as claimed in claim 1, wherein in step (ii) the compound of formula (III) is brominated with a brominating agent selected from dibromantin and N-bromosuccinamide, in presence of organic solvent selected from tetrahydrofuran, acetone, N,N-dimethyl formamide, DMSO, methanol, methylene dichloride, acetonitrile, ethyl acetate, diethyl ether, 1-butanol, methylethyl ketone, 1-propanol, and formamide, to form a compound of formula (IV).

4. The process as claimed in claim 1, wherein in step (iii) the compound of formula (IV) is debrominated to form a compound of formula (V) in the presence of a catalyst, a thiol compound of formula (VIII), and an aprotic solvent, wherein formula (VIII) is:

$R_t$—SH            Formula VIII wherein $R_t$ is —$CH_2COOH$ or —$CH_2CH_2COOH$.

5. The process as claimed in claim 4, wherein the catalyst is selected from chromous or chromium sulfate and chromous or chromium chloride or its hydrate.

6. The process as claimed in claim 4, wherein the aprotic solvent is selected from DMF, DMAC, acetone, methylene chloride, THF, acetonitrile, DMSO and mixtures thereof.

7. The process as claimed in claim 1, wherein the compound of formula (VI) is 16α-Hydroxy Prednisolone (16-HPN), wherein C-16 and C-17 is OH.

8. The process as claimed in claim 1, wherein the compound of formula (VI) is converted to a compound of formula (I) reagents selected from N-butyraldehyde, cyclohexane carboxaldehyde, sodium metabisulphite complex, isobutyryl chloride, acetone, hydrofluoric acid, isopropenyl acetate, dibromantin, select fluor, perchloric acid, 3,3-dimethyl butyryl chloride and triethylamine, or a combination thereof.

9. The process as claimed in claim 1, wherein the compound of formula (VI) is converted to a compound of formula (I) by treating with N-butyraldehyde and hydrochloric acid such that in the compound of formula (I) thus obtained, $R_1$ is —H, $R_2$ is —$CH_2CH_2CH_3$, and $R_5$ is —OH.

10. The process as claimed in claim 1, wherein the compound of formula (I) is obtained as a mixture of epimer A and epimer B, wherein the amount of epimer A is in the range of 54 to 44% w/w.

11. The process as claimed in claim 1, wherein the compound of formula (VI) is converted to a compound of formula (I) by treating with cyclohexane carboxaldehyde, sodium metabisulphite and isobutyryl chloride, such that in the compound of formula (I) thus obtained $R_1$ is —H, $R_2$ is —$C_6H_{11}$, and $R_5$ is —$OCOCH(CH_3)_2$.

12. The process as claimed in claim 1, wherein the compound of formula (VI) having $R_3$ and $R_4$ as H is converted to a compound of formula (I) by treating with acetone and perchloric acid, such that in the compound of formula (I) thus obtained $R_1$ is —$CH_3$, $R_2$ is —$CH_3$, and $R_5$ is —OH.

13. The process as claimed in claim 1, wherein the compound of formula (VI) having $R_4$ as H is converted to a compound of formula (I) by treating with acetone, dibromantin, hydrofluoric acid, such that in the compound of formula (I) thus obtained, $R_1$ is —$CH_3$, $R_2$ is —$CH_3$, $R_5$ is —OH, $R_3$ is —F, and $R_4$ is —H.

14. The process as claimed in claim 1, wherein the compound of formula (VI) having $R_3$ and $R_4$ as H is converted to a compound of formula (I) by treating with acetone, isopropenyl acetate and select fluor, such that in the compound of formula (I) $R_1$ is —$CH_3$, $R_2$ is —$CH_3$, $R_5$ is —OH, $R_3$ is —H, and $R_4$ is —F.

15. The process as claimed in claim 1, wherein the compound of formula (VI) having $R_4$ as H is converted to a compound of formula (I) by treating with perchloric acid, dibromantin, hydrofluoric acid and 3,3-dimethyl butyryl chloride such that in the compound of formula (I) thus obtained, $R_1$ and $R_2$ are —$CH_3$, $R_5$ is —OH, $R_3$ is —F, and $R_4$ is —H.

16. The process as claimed in claim 1, wherein in step (i) dihydroxylation of the compound of formula (II) is carried out with an oxidizing agent selected from potassium permanganate, formic acid, and sodium metabisulphite, to form the compound of formula (III).

17. The process as claimed in claim 1, wherein in step (ii) the compound of formula (III) is brominated with dibromatin in presence of tetrahydrofuran to obtain a compound of formula (IV).

18. The process as claimed in claim 4, wherein the thiol compound is Rt-SH wherein Rt is —$CH_2COOH$.

19. The process as claimed in claim 5, wherein the catalyst is chromium chloride hexahydrate.

20. The process as claimed in claim 4, wherein the aprotic solvent is selected from DMF, DMSO, and mixtures thereof.

* * * * *